US011369267B2

(12) United States Patent
Melodia et al.

(10) Patent No.: US 11,369,267 B2
(45) Date of Patent: Jun. 28, 2022

(54) RECONFIGURABLE IMPLANTABLE MEDICAL SYSTEM FOR ULTRASONIC POWER CONTROL AND TELEMETRY

(71) Applicant: Northeastern University, Boston, MA (US)

(72) Inventors: Tommaso Melodia, Newton, MA (US); Raffaele Guida, Boston, MA (US); Giuseppe Enrico Santagati, Cambridge, MA (US)

(73) Assignee: Northeastern University, Boston, MA (US)

( * ) Notice: Subject to any disclaimer, the term of this patent is extended or adjusted under 35 U.S.C. 154(b) by 411 days.

(21) Appl. No.: 16/345,156

(22) PCT Filed: Oct. 31, 2017

(86) PCT No.: PCT/US2017/059284
§ 371 (c)(1),
(2) Date: Apr. 25, 2019

(87) PCT Pub. No.: WO2018/081793
PCT Pub. Date: May 3, 2018

(65) Prior Publication Data
US 2019/0313908 A1    Oct. 17, 2019

Related U.S. Application Data

(60) Provisional application No. 62/415,383, filed on Oct. 31, 2016.

(51) Int. Cl.
*A61B 5/00*    (2006.01)
*A61N 1/378*    (2006.01)
(Continued)

(52) U.S. Cl.
CPC .......... *A61B 5/0031* (2013.01); *A61B 5/0015* (2013.01); *A61B 5/0028* (2013.01);
(Continued)

(58) Field of Classification Search
CPC ... A61B 5/0031; A61B 5/0015; A61B 5/0028; A61B 5/7225; A61B 2560/0219;
(Continued)

(56) References Cited

U.S. PATENT DOCUMENTS

2004/0172083 A1*    9/2004 Penner ................. A61N 1/3718
607/35
2007/0093875 A1    4/2007 Chavan et al.
(Continued)

FOREIGN PATENT DOCUMENTS

JP    2012524633 A    10/2012
WO    2010124193 A1    10/2010
(Continued)

OTHER PUBLICATIONS

Achraf Ben Amar, Ammar B Kouki, and Hung Cao. 2015. Power Approaches for Implantable Medical Devices. Sensors 15, 11 (2015), 28889-28914.
(Continued)

*Primary Examiner* — Lindsey G Wehrheim
(74) *Attorney, Agent, or Firm* — Hamilton, Brook, Smith & Reynolds, P.C.

(57) ABSTRACT

A reconfigurable implantable system for ultrasonic power control and telemetry includes a charging device that includes an ultrasonic transducer to transmit and receive ultrasonic signals transmitted through a biological body, and a signal generator to drive the ultrasonic transducer to transmit an ultrasonic charging signal through the biological body. The system further includes an implantable device configured to communicate wirelessly with the charging (Continued)

device through the biological body via an ultrasonic communication link between the implantable device and the charging device. An implantable ultrasonic transducer receives the ultrasonic charging signal from the charging device and transmits ultrasonic signals through the biological body. A power unit coupled to the ultrasonic transducer harvests energy from the received ultrasonic charging signal when the implantable device is in an energy harvesting mode. A communication unit is configured to switch the implantable device between the energy harvesting mode and an ultrasonic communication mode, and to read data from the sensing or actuation unit and transmit the data through the implantable ultrasonic transducer when the implantable device is in the ultrasonic communication mode.

32 Claims, 18 Drawing Sheets

(51) Int. Cl.
G08C 23/02 (2006.01)
H02J 7/02 (2016.01)
H02J 50/80 (2016.01)
H02J 50/15 (2016.01)

(52) U.S. Cl.
CPC .......... *A61B 5/7225* (2013.01); *A61N 1/3787* (2013.01); *G08C 23/02* (2013.01); *H02J 7/025* (2013.01); *A61B 2560/0219* (2013.01); *H02J 50/15* (2016.02); *H02J 50/80* (2016.02)

(58) Field of Classification Search
CPC ....... A61N 1/3787; G08C 23/02; H02J 7/025; H02J 50/80; H02J 50/15
See application file for complete search history.

(56) References Cited

U.S. PATENT DOCUMENTS

2014/0336474 A1    11/2014  Arbabian et al.
2017/0125892 A1*   5/2017   Arbabian ............... A61B 5/686

FOREIGN PATENT DOCUMENTS

WO    2016123047 A1    8/2016
WO    2016123069 A1    8/2016

OTHER PUBLICATIONS

Mohammadreza Ashraf and Nasser Masoumi. 2016. A ermal Energy Harvesting Power Supply With an Internal Startup Circuit for Pacemakers. IEEE Transactions on Very Large Scale Integration (VLSI) Systems 24, 1 (2016), 26-37.
Hamid Basaeri, David Christensen, Shad Roundy, Yuechuan Yu, Tram Nguyen, Prashant Tathireddy, and Darrin J Young. 2016. Ultrasonically powered hydrogel-based wireless implantable glucose sensor. In Sensors, 2016 IEEE. IEEE, 1-3.
Majid Beidaghi and Yury Gogotsi. 2014. Capacitive energy storage in micro-scale devices: recent advances in design and fabrication of micro-supercapacitors. Energy & Environmental Science 7, 3 (2014), 867-884.
Kara N Bocan and Ervin Sejdic'. 2016. Adaptive Transcutaneous Power Transfer to Implantable Devices: A State of the Art Review. Sensors 16, 3 (2016), 393.
Wayne Burleson, Sandro Carrara, and others. 2014. Security and privacy for Implantable medical devices. Springer.
Andrea Cadei, Alessandro Dionisi, Emilio Sardini, and Mauro Serpelloni. 2013. Kinetic and thermal energy harvesters for implantable medical devices and biomedical autonomous sensors. Measurement Science and Technology 25, 1 (2013), 012003.
Giuseppe Mario Calvagna, Giuseppe Torrisi, Clea Giufiida, and Salvatore Patane'. 2014. Pacemaker, implantable cardioverter defibrillator, CRT, CRT-D, psychological difficulties and quality of life. International journal of cardiology 174, 2 (2014), 378-380.
J. Charthad, M.J. Weber, Ting Chia Chang, M. Saadat, and A. Arbabian. A mm-sized implantable device with ultrasonic energy transfer and RF data uplink for high-power applications. In Proc. of IEEE Custom Integrated Circuits Conference (CICC), pp. 1-4, Sep. 2014.
Wenwen Chen, Guozheng Yan, Shu He, an Ke, Zhiwu Wang, Hua Liu, and Pingping Jiang. 2013. Wireless powered capsule endoscopy for colon diagnosis and treatment. Physiological measurement 34, 11 (2013), 1545.
Alexey Denisov and Eric Yeatman. 2010. Ultrasonic vs. inductive power de-livery for miniature biomedical implants. In Body Sensor Networks (BSN), 2010 International Conference on. IEEE, 84-89.
Tamara Denning, Alan Borning, Batya Friedman, Brian T Gill, Tadayoshi Kohno, and William H Maisel. 2010. Patients, pacemakers, and implantable defibrillators: Human values and security for wireless implantable medical devices. In Proceedings of the SIGCHI Conference on Human Factors in Computing Systems. ACM, 917-926.
Frank D Egitto, Rabindra N Das, Glen E Thomas, and Susan Bagen. 2012. Miniaturization of electronic substrates for medical device applications. In International Symposium on Microelectronics, vol. 2012. International Microelectronics Assembly and Packaging Society, 000186-000191.
Laura Galluccio, Tommaso Melodia, Sergio Palazzo, and Giuseppe Enrico Santagati. 2012. Challenges and Implications of using ultrasonic communications in intra-body area networks. In Wireless On-demand Network Systems and Services (WONS), 2012 9th Annual Conference on. IEEE, 182-189.
Michael R Gold. 2015. Are Leadless Pacemakers a Niche or the Future of Device therapy? Journal of the American College of Cardiology 15, 65 (2015), 1505-1508.
Erik O Udo, Norbert M van Hemel, Nicolaas PA Zuitho , Heidi Nijboer, William Taks, Pieter A Doevendans, and Karel GM Moons. 2013. Long term quality-of-life in patients with bradycardia pacemaker implantation. International journal of cardiology 168, 3 (2013), 2159-2163.
Raffaele Guida, G Enrico Santagati, and Tommaso Melodia. 2016. A 700 kHz ultrasonic link for wireless powering of implantable medical devices. In Sensors, 2016 IEEE. IEEE, 1-3.
Mahammad A Hannan, Saad Mutashar, Salina A Samad, and Aini Hussain. 2014. Energy harvesting for the implantable biomedical devices: issues and challenges. Biomed. Eng. Online 13, 1 (2014), 79.
ULTRAsponder. 2008. Invivo Ultrasonic Transponder System for Biomedical Applications Invivo Ultrasonic Transponder System. (2008). Retrieved Mar. 9, 2017 from http://www.ultrasponder.org/project/project.html.
Rangarajan Jegadeesan, Kush Agarwal, Yong-Xin Guo, Shih-Cheng Yen, and Nitish V Thakor. 2016. Wireless Power Delivery to Flexible Subcutaneous Implants Using Capacitive Coupling. IEEE Transactions on Microwave Theory and Techniques (2016).
Yeun-Ho Jounge. 2013. Development of implantable medical devices: from an engineering perspective. International neurourology journal 17, 3 (2013), 98-106.
M Amin Karami and Daniel J Inman. 2012. Powering pacemakers from heartbeat vibrations using linear and nonlinear energy harvesters. Applied Physics Letters 100, 4 (2012), 042901.
Mehdi Kiani and Maysam Ghovanloo. 2012. The circuit theory behind coupled mode magnetic resonance-based wireless power transmission. IEEE Transactions on Circuits and Systems I: Regular Papers 59, 9 (2012), 2065-2074.
Albert Kim, Manuel Ochoa, Rahim Rahimi, and Babak Ziaie. 2015. New and Emerging Energy Sources for Implantable Wireless Microdevices. Access, IEEE 3 (2015), 89-98.
Asimina Kiourti and Konstantina S Nikita. 2012. A review of implantable patch antennas for biomedical telemetry: Challenges

(56) References Cited

OTHER PUBLICATIONS and solutions [wireless corner]. IEEE Antennas and Propagation Magazine 54, 3 (2012), 210-228.
Asimina Kiourti, Konstantinos A Psathas, and Konstantina S Nikita. 2014. Im-plantable and ingestible medical devices with wireless telemetry functionalities: A review of current status and challenges. Bioelectromagnetics 35, 1 (2014), 1-15.
Chu-Pak Lau, Chung-Wah Siu, and Hung-Fat Tse. 2014. Future of implantable devices for cardiac rhythm management. Circulation 129, 7 (2014), 811-822.
Bert Lenaerts and Robert Puers. 2009. Omnidirectional inductive powering for biomedical implants. Springer.
Ye-Sing Luo, Jiun-Ru Wang, Wei-Jen Huang, Je-Yu Tsai, Yi-Fang Liao, Wan-Ting Tseng, Chen-Tung Yen, Pai-Chi Li, and Shen-Iuan Liu. 2013. Ultrasonic power/data telemetry and neural stimulator with OOK-PM signaling. IEEE Transactions on Circuits and Systems II: Express Briefs 60, 12 (2013), 827-831.
E Meng and R Sheybani. 2014. Insight: implantable medical devices. Lab on a Chip 14, 17 (2014), 3233-3240.
Giuseppina Monti, Paola Arcuti, and Luciano Tarricone. 2015. Resonant Inductive Link for Remote Powering of Pacemakers. Microwave theory and Techniques, IEEE Transactions on 63, 11 (2015), 3814 3822.
K Murali, N Scianmarello, and MS Humayun. 2015. Harvesting solar energy to power ocular implants. In Biomedical Circuits and Systems Conference (BioCAS), 2015 IEEE. IEEE, 1-4.
Ufuk Muncuk, Prusayon Nintanavongsa, David Richard Lewis, and Kaushik Roy Chowdhury. 2012. Design optimization and implementation for RF energy harvesting circuits. IEEE Journal on emerging and selected topics in circuits and systems 2, 1 (2012), 24-33.
Jacopo Olivo, Sandro Carrara, and Giovanni De Micheli. 2011. Energy harvesting and remote powering for implantable biosensors. IEEE Sensors Journal 11, EPFL-Article-152140 (2011), 1573-1586.
Shaul Ozeri and Doron Shmilovitz. 2014. Simultaneous backward data transmission and power harvesting in an ultrasonic transcutaneous energy transfer link employing acoustically dependent electric impedance modulation. Ultrasonics 54, 7 (2014), 1929-1937.
Shaul Ozeri, Doron Shmilovitz, Sigmond Singer, and Chua-Chin Wang. 2010. Ultrasonic transcutaneous energy transfer using a continuous wave 650kHz Gaussian shaded transmitter. Ultrasonics 50, 7 (2010), 666-674.
Yang Yang, Guo Dong Xu, and Jing Liu. 2014. A prototype of an implantable thermoelectric generator for permanent power supply to body inside a medical device. Journal of Medical Devices 8, 1 (2014), 014507.
R Puers, Riccardo Carta, and Jef one'. 2011. Wireless power and data transmission stralegies for next-generation capsule endoscopes. Journal of Micromechanics and Microengineering 21, 5 (2011), 054008.
Leon Radziemski and Inder Raj S Makin. 2016. In vivo demonstration of ultrasound power delivery to charge implanted medical devices via acute and survival porcine studies. Ultrasonics 64 (2016), 1-9.
Smitha Rao and J-C Chiao. 2015. Body Electric: Wireless Power Transfer for Implant Applications. Microwave Magazine, IEEE 16, 2 (2015), 54 64.

Mahdi Rasouli and Louis Soo Jay Phee. 2010. Energy sources and their development for application in medical devices. Expert review of medical devices 7, 5 (2010), 693-709.
G. E. Santagati and T. Melodia. 2017. An Implantable Low-Power Ultrasonic Plat-form for the Internet of Medical Things. In Proc. of IEEE Conference on Computer Communications (INFOCOM) Atlanta, USA.
Ozeri Shaul and Shmilovitz Doron. 2012. Non-invasive sensing of the electrical energy harvested by medical implants powered by an ultrasonic transcutaneous energy transfer link. In Industrial Electronics (ISIE), 2012 IEEE International Symposium on. IEEE, 1153-1157.
Jan Smilek and Zdenek Hadas. 2015. A study of kinetic energy harvesting for biomedical application in the head area. Microsystem Technologies (2015), 1-13.
Svilainis and G Motieju ñas. 2016. Power amplifier for ultrasonic transducer excitation. Ultragarsas Ultrasound 58, 1 (2016), 30-36.
J-Y Tsai, K-H Huang, J-R Wang, S-I Liu, and P-C Li. 2011. Ultrasonic wireless power and data communication for neural stimulation. In Ultrasonics Symposium (IUS), 2011 IEEE International. IEEE, 1052-1055.
Zian H Tseng, Robert M Hayward, Nina M Clark, Christopher G Mulvanny, Benjamin J Colburn, Philip C Ursell, Jeffrey E Olgin, Amy P Hart, and Ellen Moffatt. 2015. Sudden death in patients with cardiac implantable electronic devices. JAMA internal medicine 175, 8 (2015), 1342-1350.
International Search Report and Written Opinion for International Application No. PCT/US2017/059284 entitled "Reconfigurable Implantable Medical System for Ultrasonic Power Control and Telemetry," dated Feb. 1, 2018.
Mazzilli, et al., "3.2 mW Ultrasonic LSK Modulator for Uplink Communication in Deep Implanted Medical Devices," 2014 IEEE Biomedical Circuits and Systems Conference (BIOCAS) Proceedings, IEEE, pp. 636-639 (Oct. 22, 2014).
A. Toprak and O. Tigli, "Piezoelectric energy harvesting: State-of-the-art and challenges," Applied Physics Reviews, vol. 1, No. 3, p. 031104, 2014.
G. Santagati, T. Melodia, L. Galluccio, and S. Palazzo, "Medium access control and rate adaptation for ultrasonic intra-body sensor networks," IEEE/ACM Transactions on Networking, vol. 23, pp. 1121-1134, Aug. 2015.
G. E. Santagati and T. Melodia, "U-wear: Software-defined ultrasonic networking for wearable devices," in Proceedings of the 13th Annual International Conference on Mobile Systems, Applications, and Services, pp. 241-256, ACM, 2015.
R. Phillips and G. Harris, "Information for manufacturers seeking marketing clearance of diagnostic ultrasound systems and transducers," Food and Drug Administralion, Center for Devices and Radiological Health, 2008.
E. Demirors, G. Alba, G. E. Santagati, and T. Melodia, "High Data Rate Ultrasonic Communications for Wireless Intra-Body Networks," in Proc. of IEEE Symposium on Local and Metropolitan Area Networks (LANMAN), (Rome, Italy), Jun. 2016.
Piezo Products & Materials Supplier / APC International, https://www.americanpiezo.com—accessed Jun. 6, 2019.
Notification Concerning Transmittal of International Preliminary Report on Patentability re International Application No. PCT/US2017/059284 entitled "Reconfigurable Implantable Medical System for Ultrasonic Power Control and Telemetry," dated May 9, 2019.

\* cited by examiner

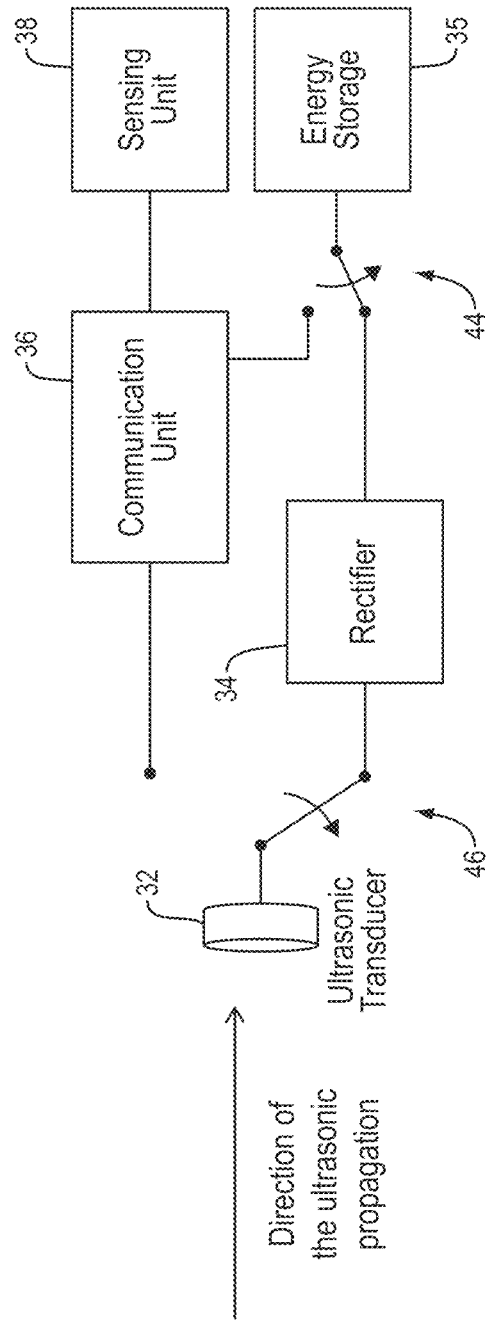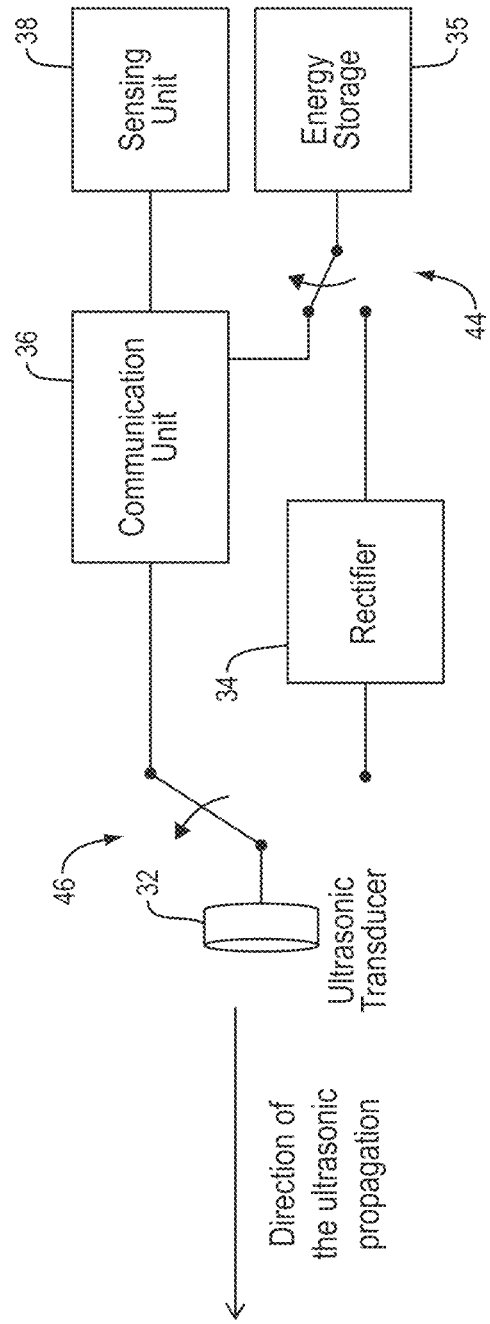

RECONFIGURABLE IMPLANTABLE MEDICAL SYSTEM FOR ULTRASONIC POWER CONTROL AND TELEMETRY

RELATED APPLICATIONS

This application is the U.S. National Stage of International Application No. PCT/US2017/059284, filed on Oct. 31, 2017, which designates the U.S., published in English, and claims the benefit of U.S. Provisional Application No. 62/415,383, filed on Oct. 31, 2016. The entire teachings of the above applications are incorporated herein by reference.

GOVERNMENT SUPPORT

This invention was made with government support under Grant No. CNS-1253309 from the National Science Foundation. The government has certain rights in the invention.

BACKGROUND

A variety of medical implantable devices (IMDs) have been developed in recent years that provide life-saving functionalities and enhance patients' quality of life. One challenging aspect faced by both traditional systems and future designs is how to power or recharge an implanted device under constraints on miniaturization while complying with low power levels allowed by the Food and Drug Administration (FDA). The next generation of implanted devices is expected to be endowed with wireless communication, sensing, processing, and actuation capabilities, which will increase the power requirements even more.

SUMMARY

A reconfigurable implantable system and associated method for ultrasonic power control and telemetry is provided.

In an embodiment, the system includes a charging device and an implantable device. The charging devices includes an ultrasonic transducer configured to transmit ultrasonic signals and to receive ultrasonic signals transmitted through a biological body, and a signal generator to drive the ultrasonic transducer to transmit an ultrasonic charging signal through the biological body. The implantable device is implantable in the biological body and is configured to communicate wirelessly with the charging device through the biological body via an ultrasonic communication link between the implantable device and the charging device. The implantable device includes: an implantable ultrasonic transducer to receive the ultrasonic charging signal from the charging device and to transmit ultrasonic signals through the biological body; a power unit coupled to the ultrasonic transducer, the power unit configured to harvest energy from the received ultrasonic charging signal when the implantable device is in an energy harvesting mode; a sensing or actuation unit powered by the harvested energy; and a communication unit coupled to the power unit and the sensor or actuation unit. The communication unit is configured to switch the implantable device between the energy harvesting mode and an ultrasonic communication mode. The communication unit is further configured to read data from the sensing or actuation unit and transmit the data through the implantable ultrasonic transducer when the implantable device is in the ultrasonic communication mode.

The power unit can include rectifying circuitry capable of converting an alternating current (AC) signal from the implantable ultrasonic transducer to a direct current (DC) signal. The rectifying circuitry can include a multiplier. In some embodiments, the power unit includes a multiplier and a full wave rectifier. Depending on the power of the ultrasonic charging signal, the power unit may choose to use the multiplier or the full wave rectifier.

The power unit can include an energy storage unit coupled to the rectifying circuitry to store the harvested energy. The energy storage unit can include a supercapacitor.

The power unit can includes a low drop out (LDO) regulator to limit the output voltage from the energy storage unit. This may limit the amount of energy that can be used from the storage unit.

At least one of the communication unit and the sensing or actuation unit can include programmable circuitry. Programmable circuitry can include a field programmable gate array (FPGA) that is programmable via the ultrasonic communication link while the implantable device is implanted.

The sensing or actuation unit can include or communicate with a sensor, an actuator, or both, and the FPGA can be programmed to control the sensor, the actuator, or both. Alternatively or in addition, the communication unit can include a microcontroller unit (MCU). The sensing or actuation unit can include or communicate with an actuator, a sensor, or both, and the MCU can be configured to control the actuator, the sensor, or both.

The charging device can be wearable on the biological body. Alternatively, the charging device is implantable in the biological body.

The signal generator of the charging device can provide an electric signal, and the charging device can further include an amplifier to amplify the electric signal to drive the ultrasonic transducer of the charging device.

The frequency of the ultrasonic charging signal can be in a range of about 20 kHz to about 10 MHz. The ultrasonic charging signal can include a continuous wave, such as a continuous sine wave or a continuous square wave. In an embodiment, the frequency of the of the continuous wave is around 700 kHz.

After energy harvesting, the implantable device can be configured using a control channel of the ultrasonic communication link to adapt one or more of (i) ultrasonic transmission operations, (ii) data processing operations performed on the data, and (iii) sensing operations performed by the sensing or actuation unit.

For example, after energy harvesting, the implantable device can be configured using a control channel of the ultrasonic communication link to adapt ultrasonic transmission operations by changing the transmission scheme parameters to adapt to the intra-body channel conditions, or to adapt data processing operations by performing one or more of modifying processing features and extracting new physiological parameters from the data, or to adapt sensing operations by changing the sampling frequency of a sensor or the sensing resolution of the sensor. Modifying processing operations can include installing new processing features.

In an embodiment, the system comprises plural implantable devices.

A method for ultrasonic power control and telemetry includes a) transmitting ultrasonic signals through a biological body via an ultrasonic communication link between a charging device and an implantable device implanted in the biological body; b) with an ultrasonic transducer of the implantable device, receiving an ultrasonic charging signal from the charging device; c) harvesting energy from the received ultrasonic charging signal when the implantable device is in an energy harvesting mode; d) powering a sensing or actuation unit of the implantable device with the harvested energy; and e) reading data from the sensing or actuation unit and transmitting the data through the ultrasonic transducer of the implantable device when the implantable device is in the ultrasonic communication mode.

The method can further include, in the charging device, driving an ultrasonic transducer to transmit the ultrasonic charging signal through the biological body.

The method can further include, in the implantable device, converting an alternating current (AC) signal output from the ultrasonic transducer to a direct current (DC) signal using rectifying circuitry.

The method can further include storing the harvested energy in an energy storage unit of the implantable device.

The method can further include programming a field programmable gate array (FPGA) of the implantable device via the ultrasonic communication link while the implantable device is implanted.

The method can further include switching the implantable device between the energy harvesting mode and the ultrasonic communication mode.

The method can further include, after energy harvesting, configuring the implantable device using a control channel of the ultrasound communication link to adapt one or more of (i) ultrasonic transmission operations, (ii) data processing operations performed on the data, and (iii) sensing operations performed by the sensing or actuation unit.

A reconfigurable implantable device for ultrasonic power control and telemetry is provided. The implantable device is implantable in a biological body and configured to communicate wirelessly with a charging device through the biological body via an ultrasonic communication link between the implantable device and the charging device. The implantable device includes: an implantable ultrasonic transducer to receive an ultrasonic charging signal from the charging device and to transmit ultrasonic signals through the biological body; a power unit coupled to the ultrasonic transducer, the power unit configured to harvest energy from the received ultrasonic charging signal when the implantable device is in an energy harvesting mode; a sensing or actuation unit powered by the harvested energy; and a communication unit coupled to the power unit and the sensor or actuation unit. The communication unit is configured to switch the implantable device between the energy harvesting mode and an ultrasonic communication mode, and to read data from the sensing or actuation unit and transmit the data through the implantable ultrasonic transducer when the implantable device is in the ultrasonic communication mode.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 3 illustrates an energy harvesting mode of an implantable device.

FIG. 4 illustrates an ultrasonic communication mode of the implantable device of FIG. 3.

DETAILED DESCRIPTION

Figure 1:
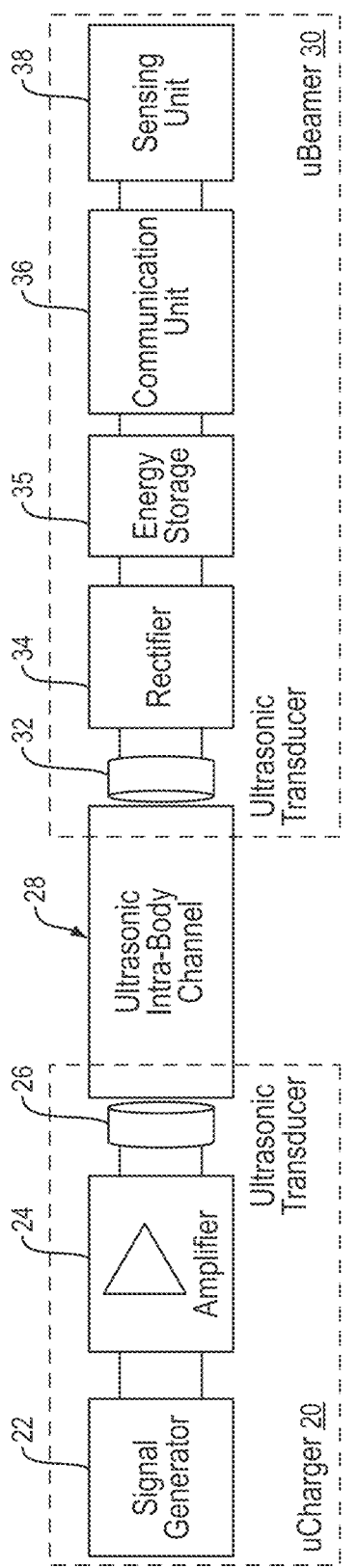
FIG. 1 is a component diagram of an ultrasonic wireless powering and telemetry system according to an example embodiment of the invention.

A description of example embodiments follows.

A reconfigurable implantable medical system and method are provided to enable wireless ultrasonic power control and telemetry via an intra-body communication link.

A prior ultrasonic network for wearable devices is described in International Application No. PCT/US2016/014814, by Melodia et al., filed Jan. 26, 2016, and published as WO 2016/123047 A1, the entire teachings of which are incorporated herein by reference.

A prior system and method for transmitting signals ultrasonically among a network of implantable and wearable devices are described in International Application No. PCT/US2016/014860, by Melodia et al., filed Jan. 26, 2016, and published as WO2016/123069 A1, the entire teachings of which are incorporated herein by reference.

With respect to the previous approaches, the current approach provides a system uniquely designed to manage energy, power transmission efficiency, and circuit interconnections to address the challenges that arise from combining a reconfigurable ultrasonic communication module with an ultrasonic, remotely powered implantable device.

Batteryless System.

Embodiments of the present invention relate to a batteryless system that utilizes an ultrasonic transcutaneous energy transfer (UTET) method to charge one or more supercapacitors (storage unit) that provide energy to the implantable device. Furthermore, the implantable device can utilize a battery in addition to the supercapacitors or to substitute them. However, the present system is primarily designed to work without a battery. This aspect introduces challenges and problems that are not present in a system with a battery, whether the battery is rechargeable or not.

In a battery powered system, energy is not as constrained as in a system that uses UTET and supercapacitors. In fact, a battery can provide enough energy to perform several functionalities, including reconfiguration through programmable circuitry (e.g., an FPGA), reading of sensed data, and actuation, without the need to recharge the device in between.

In a batteryless system, energy consumption and power management become major challenges. Generally, only one or a few consecutive operations, including reconfiguration, data processing and transfer, are typically possible before energy storage is depleted. Hence, every operation or every few operations of the system typically have to be preceded by a charging cycle. Thus, charging is more frequent, but at the same time, it can be faster than battery recharging.

When considering a reconfigurable module (e.g., an implanted device) powered by a UTET-based power unit, it is useful to consider how the two subsystems interact with each other. From the circuital point of view, the design must consider two different modes of operations, the charging phase and the following sensing/actuation/communication phase, and the relative electrical connections and how to switch from one circuit configuration to the other (as explained elsewhere). As for the energy management, the following considerations have to be taken into account. On the one hand, the UTET method can provide the energy necessary only to reconfigure the implant and a few other operations; hence, the frequency and duration of the recharging phases become key aspects. On the other hand, the reconfigurability of the implant impacts the power unit design and the energy management in at least two ways:

- by changing how energy is re-distributed to power the electronic circuitry of the implant, or by adjusting the power requirements of the components following a specific configuration;
- by changing parameters (e.g., low dropout (LDO) regulator threshold), data processing algorithms, sensing/actuation frequency, circuit connections, with a resulting power consumption that can differ from case to case, leading ultimately to more or less frequent recharging operations.

Based on these observations, it is useful to optimize the system design for the charging phase, so that the power transfer efficiency (PTE) can be maximized to convey as much power as possible from the remote transmitter to the storage. Conversely, the supercapacitor output power, which is used to execute sensing/actuation/communication, is preferably limited, first to save energy and, second, to meet voltage and current requirements of the components that it powers. Specifically, the LDO regulator limits the output voltage from the storage unit to the load, the microcontroller and FPGA manage the powering for intermittent sensing and periodic actuation operations, or to perform them when required.

Direct Powering.

The ultrasonically transferred energy can be used directly (without being stored) to activate a sensor, an actuator, a communication unit, or to power the communication circuitry on the implanted device to receive instantaneous replies to queries sent by the transmitter. In the case of direct powering, the low dropout (LDO) regulator can be used to reduce the incoming rectified voltage and power the load.

I. Introduction

Powering implanted electronic systems is a critical challenge in the area of implantable medical devices (IMDs) [A1] [A2]. Clearly, this is a crucial problem especially for life-saving medical devices like cardiac or neural bio-implants. Currently, the most common ways to provide the energy necessary to power IMDs are batteries and supercapacitors, energy harvesting solutions, and Transcutaneous Energy Transfer (TET). Among the different TET technologies, which include radio frequency (RF) transmission and electromagnetic induction [2], ultrasonic TET (UTET) is particularly promising [A3] [A4] [A5], [A6].

Ultrasounds traversing biological tissues can result in phenomena such as cavitation, mechanical stimulation, and temperature increase. In specific cases, depending on the power of the acoustic wave and the duration of the exposure, health hazards can arise. For these reasons, the FDA regulates the acoustic wave power emissions defining the safety limits for ultrasound transmissions in medical applications [A7]. The safety limitations on acoustic power are, however, less constraining with respect to RF radiation exposure limits [A6]. The benefits of using ultrasounds can therefore be grouped in three major categories briefly described below.

Safety.

Exposure of human tissues to ultrasounds is considered safer than exposure to electromagnetic (EM) radiations. EM waves are significantly absorbed by vital organs (particularly by cardiac and brain tissues) and, as a consequence, the temperature in the exposed area of the body increases and the power transferred to the receiver end of a wireless RF link is significantly reduced.

Power Levels.

Higher power intensities can be used for ultrasonic transmissions with no health hazards. For this reason, the FDA allows much higher intensity for acoustic waves (720 mW/cm$^2$) in tissues as compared to RF (10 mW/cm$^2$), i.e., almost two orders of magnitude higher.

Propagation in Human Tissues.

The significantly lower absorption by biological tissues of ultrasonic waves (e.g., 8-16 dB for a 10-20 cm link at 1 MHz, vs 60-90 dB at 2.45 GHz as used in Bluetooth) results in much reduced tissue heating, which makes propagation safer. Furthermore, from a technical point of view, this means that the power losses by absorption are reduced. UTET power transmission efficiency has been reported to be as high as 39%. In addition, there are no electromagnetic compatibility concerns with a crowded RF spectrum. Therefore, wireless powering of or recharging of batteries in deep implants via ultrasounds can be much faster than alternative solutions. As a consequence, batteryless and battery powered implants can last longer or be smaller in size.

Described is here a system that uses ultrasonic waves for remote wireless powering, as well as for digital wireless communications. The system includes an Ultrasonic Trans-cutaneous Energy Transmission (UTET) link for deeply implanted medical devices, where the receiver is able to harvest energy from an ultrasonic transmitter to charge an energy storage, e.g., a battery or a supercapacitor.

II. Features

In certain embodiments, the system includes the following advantageous features:

The implantable device communicates via ultrasounds and is powered through an Ultrasonic Trans-cutaneous Energy Transfer (UTET) method by using a single piezoelectric transducer.

The system is configured to be fully and on-the-fly reconfigurable. In fact, after energy transmission, the device can be configured using a control channel to flexibly adapt (i) the transmission operations, e.g., the transmission scheme parameters to adapt to the intra-body channel conditions; (ii) the data processing operations done on the sensed data, e.g., install new processing features and extract new physiological parameters; (iii) the sensing operations, e.g., the sampling frequency of the sensor or the sensing resolution, among others.

III. System Description

FIG. 1 shows the component diagram of a reconfigurable implantable system 10 for ultrasonic power control and telemetry. The component blocks on the left of the figure represent the charging device 20 (also referred to herein as "uCharger"), which can be an external, e.g., outside the body, device. Device 20 powers the implantable device 30 or recharges the implantable device battery, as well as receives data transmitted by the implantable device 30. Power and data transmission are accomplished via an ultrasonic intra-body communication link 28 between devices 20 and 30. The device 20 includes a signal generator 22, e.g., a USRP N210 software defined radio in this implementation, which generates the waveform, followed by an amplifier 24 and a piezoelectric transducer (PZT) 26. The device 20 can be an always-on wearable device attached to the user's skin, or a handheld device. The implantable component 30 (also referred to herein as "uBeamer") implements both energy harvesting and wireless communication functionalities. When harvesting energy transmitted by the charging device 20, the implantable device 30 receives ultrasonic waves through the ultrasonic transducer 32, rectifies the electrical signal corresponding to the received ultrasonic waves using rectifier 34, and, optionally, stores the incoming energy into energy storage 35, e.g., a battery or a supercapacitor. Once enough energy has been harvested, the implantable component 30 activates a sensing or actuation unit 38 and a communication unit 36. The sensing or actuation unit 38, which can include or communicate with a sensor, can be configured to measure physiological parameter(s) inside the user's (i.e., the human) body. The measured parameter(s) can then be broadcasted using ultrasonic waves, e.g., via ultrasonic transducer 32, and received by another device, e.g., by device 20 via ultrasonic transducer 26. The sensing or actuation unit can also include or communicate with an actuator, e.g., a cardiac pacing lead, as further described herein.

The charging device 20 can be wearable on the biological body. In an embodiment, the charging device 20 is implantable in the biological body, in which case the device itself can be powered wireless from a base unit, e.g., via ultrasound or other suitable energy transfer means. In an embodiment, the system comprises plural implantable devices, which can be arranged in a network. A network of plural implanted devices is described, for example, in International Application No. PCT/US2016/014860 (published as WO 2016/123069 A1), the entire teachings of which are incorporated herein by reference.

A. Ultrasonic Transcutaneous Energy Transfer

The Ultrasonic Trans-cutaneous Energy Transfer (UTET) link uses two ultrasonic transducers, e.g., transducers 26 and 32 (FIG. 1), operating at the same frequency. In an example embodiment, two thin disk ultrasonic transducers (American Piezo Corporation [A10]) with a diameter of 9.5 mm are used. The two ultrasonic transducers can be geometrically aligned to minimize lateral shift (see [A9]) and, therefore, maximize the energy transfer. Ultrasonic phantoms can be used to emulate the body tissue between the uCharger 20 and the uBeamer 30. Ultrasonic phantoms are tissues mimicking materials that emulate the acoustic wave propagation through tissues. The transmission voltage signal at the external transmitter can be a continuous wave, e.g., sine or square wave, an impulsive waveform, or combination thereof. In an example implementation, the transmission signal is a continuous sine wave at 700 kHz, i.e., the resonance frequency of the transducers in use. In a particular implementation, the transmission signal is generated by a USRP N210 software defined radio, and the signal is amplified using a power amplifier, e.g., a Mini-Circuits LZY-22+ amplifier. The amplification stage is useful, and in some cases necessary, to increase the output power of the USRP, which is 2 V (peak-to-peak), to a power level that is compatible with the intra-body energy transfer application requirements. The power-amplifier signal is converted by the ultrasonic transducer (e.g., transducer 26) into an ultrasonic signal, i.e., mechanical vibrations, that propagate through the tissues, e.g., the ultrasonic phantom, and is received by the receiving ultrasonic transducer (e.g., transducer 32). The latter converts the received ultrasonic waveform into an electric signal. In order to store the energy carried by the received signal, a full wave diode rectifier (e.g., rectifier 34) is used that converts the AC signal to DC voltage level. Smoothing capacitors can be used to reduce the ripple of the rectified signal. Finally, the rectified DC voltage is used to charge an energy storage device (e.g., storage 35), such as a 0.22 F supercapacitor in an example implementation described herein.

B. Implantable "uBeamer" Device Architecture

The implantable device recalls the implementation of an active RFID device with the exception that the powering source is an ultrasonic transmitter. The implantable device can include or be connected to a sensor that acquires physiological data from the body and is powered by the energy storage once it has reached a sufficient level of charge.

Figure 2:
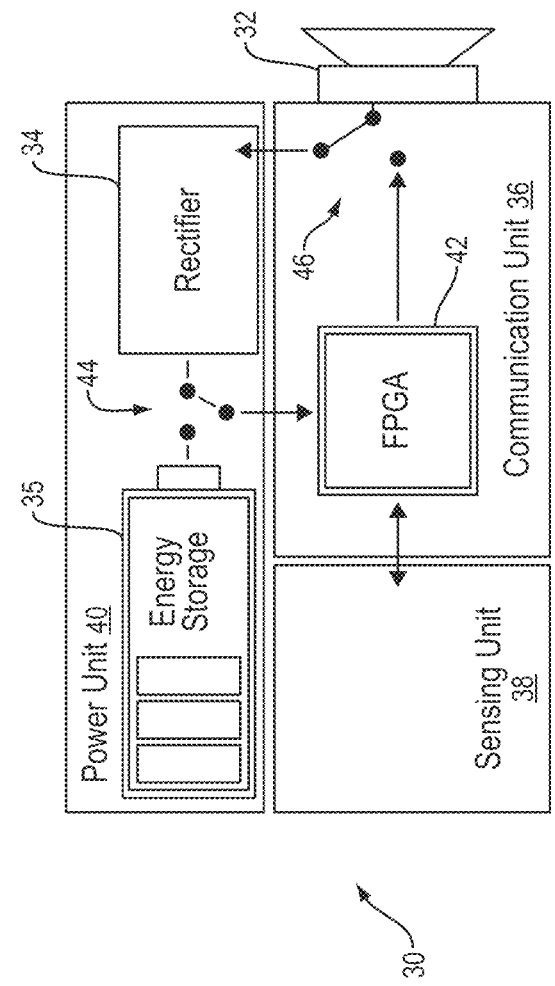
FIG. 2 is a component diagram of an implantable device of the ultrasonic wireless powering and telemetry system according to an example embodiment.

FIG. 2 shows the hardware architecture of the implantable device (uBeamer) 30. The device 30 includes a communication unit 36, an ultrasonic wireless transceiver 32 coupled to the communication unit, a sensing or actuation unit 38 (which can include, e.g., a sensor, an actuator, or both), and a power unit 40 that can include the harvesting circuit 34 and the energy storage 35. Two electronic switches 44, 46 are used to switch from charging state to communication state. The switches can be controlled by the communication unit.

FIGS. 3 and 4 show the implantable device 30 during energy harvesting operation and communication operation, respectively. As illustrated in FIG. 3, during the charging operation, switches 46 and 44 are set so that the receiver transducer 32 is connected directly to the rectifier 34, which then is connected to the energy storage 35, e.g., the supercapacitor, if present. For the backwards communication to take place, the switches 44, 46 isolate the rectifier circuit 34, and bridge the energy storage 35 and the ultrasonic transducer 32 with the communication unit 36 to power the system 30 and enable ultrasonic communication. Switches 44, 46 can be implemented in hardware or in software.

IV. Hardware Architecture of the Implantable Device

Retuning to FIG. 2, a component diagram of an implantable device 30 of the ultrasonic wireless powering and telemetry system is presented according to an example embodiment.

Communication Unit.

The communication unit 36 of the implantable device 30 includes a processing device 42, e.g., a MCU or an FPGA, which implements the ultrasonic transceiver to enable communication data processing operations. In a particular implementation, a Lattice Semiconductor iCE40 Ultra FPGA, which is currently the smallest, lowest power, and most integrated FPGA available on the market, is used. The HDL design on the FPGA initializes as soon as power is detected, switches the system from energy harvesting mode to ultrasonic communication mode, reads the sensor data through the sensing or actuation unit 38, and transmits the sensed data through the ultrasonic transducer 32.

Sensing/Actuation Unit.

The sensing or actuation unit 38 is a general-purpose interface that allows connecting different sensors, e.g., pressure and glucose sensors, and actuators to the "uBeamer" device 20 through a set of standard interfaces. The sensing or actuation unit can accommodate both digital and analog sensors.

Power Unit.

The power unit 40 includes (i) the energy harvesting circuit 34, e.g., a full wave diode rectifier with smoothing capacitors that converts the AC signal to DC voltage level, and (ii) the energy storage 35, e.g., a supercapacitor or, optionally a battery.

V. System Evaluation and Experimental Results

The output of the bridge rectifier is a critical point in the entire link, for its output voltage and current (and more in general power) determine how much and how fast the supercapacitor can be charged. To test the behavior described above, the system was excited with a sine wave oscillating at 700 kHz and at different amplitude values, up to 400 mV.

Experiments were conducted to study the system with four USRP-generated waves respectively of 300 mV, 400 mV, 700 mV and 800 mV (all peak-to-peak) to which correspond the following peak-to-peak values at the receiving ultrasonic transducer (e.g., PZT) connected to an open circuit: 10 V, 11.8 V, 23.5 V, 26 V. Also measured were the values after the amplifier, and a gain varying between 38 dB and 40 dB, depending on the input signal, was observed. This means that the attenuation in the body tissue, the transducers conversion inefficiency, and the losses due to the mismatch and misalignment between the two transducers summed up to a value between 9.3 dB and 9.5 dB. The wave is further attenuated during the rectification process, but the impact of the loss is negligible with respect to the attenuation phenomena mentioned above.

Figure 5:
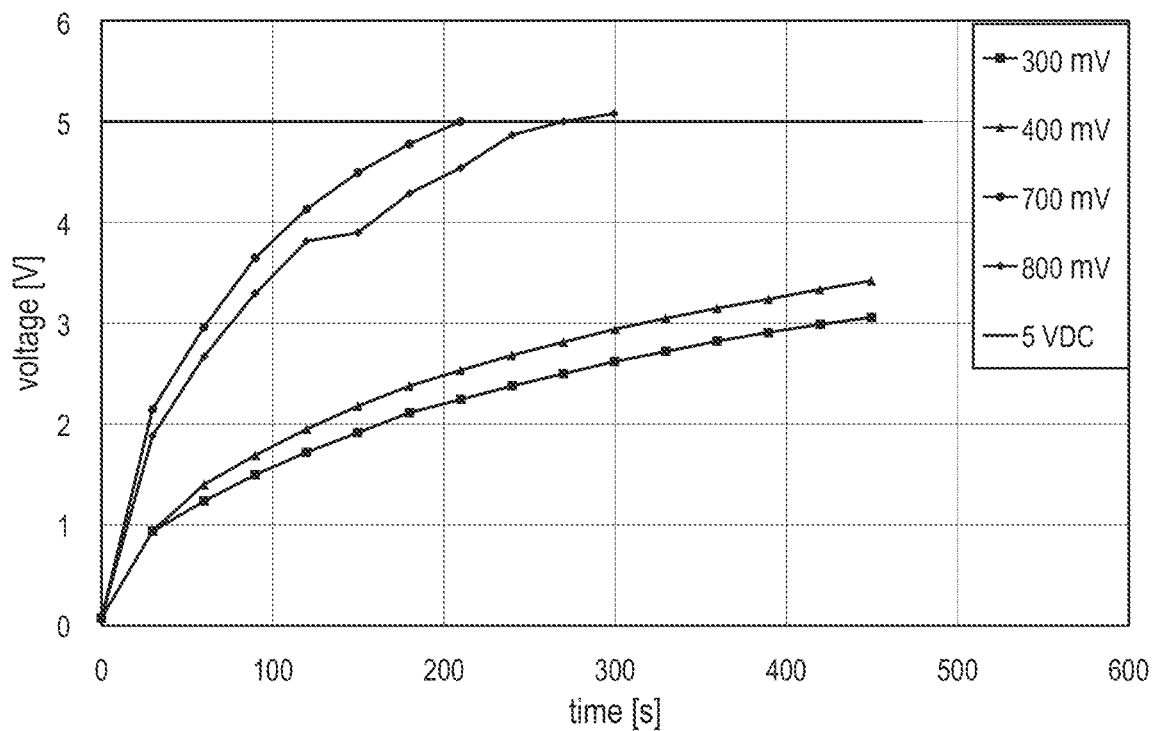
FIG. 5 illustrates voltage drops over a supercapacitor during charging.
Figure 6:
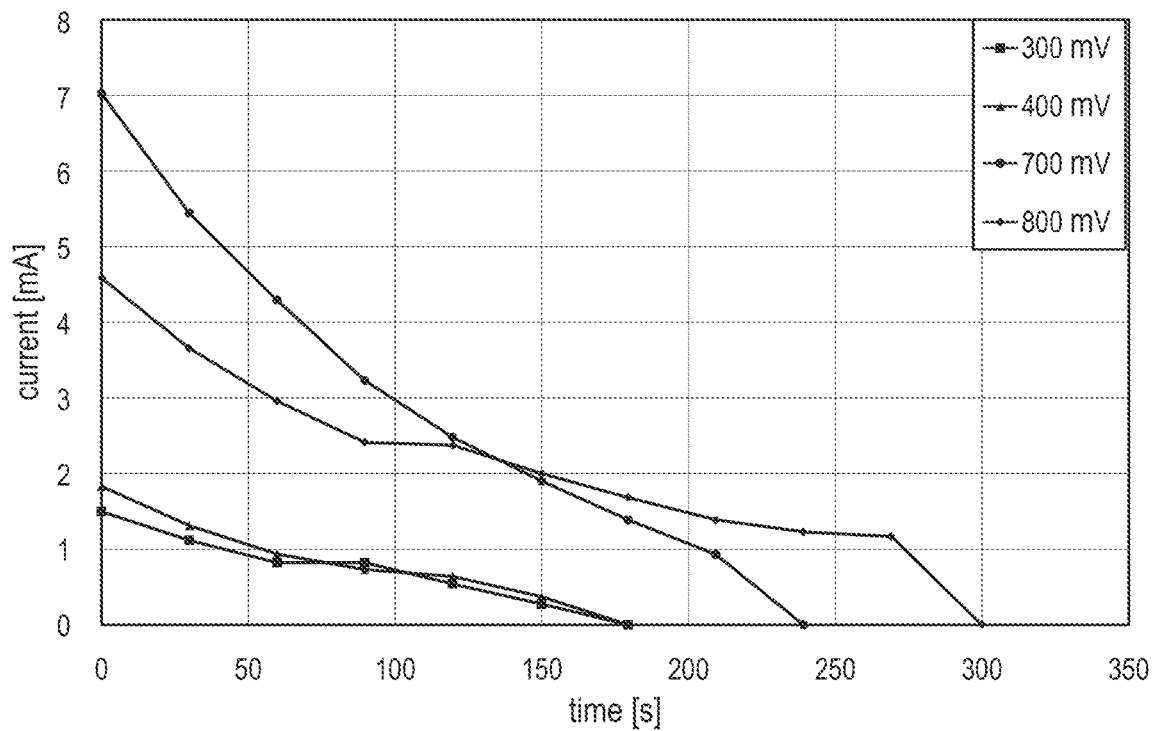
FIG. 6 illustrates input currents to the supercapacitor during charging.

In FIG. 5 and FIG. 6, the voltage drops across the supercapacitor and its input currents measured as functions of time and for different amplitude values of the USRP input waves are reported. The voltage is indicative of the charge accumulated inside the storage element, since the capacitor equation holds.

From these curves, it can be observed that increasing the input voltage to the system is not always the best strategy to recharge the capacitor faster. In fact, what determines the speed of the charging process is the current, and, in FIG. 6 it can be seen that the current corresponding to the 700 mV peak-to-peak USRP input wave is initially higher than the current flowing into the supercapacitor with the 800 mV peak-to-peak signal. As a consequence the charging in the first case reaches the 5 VDC threshold (maximum value allowed by the supercapacitor) 150 s earlier. For lower voltage values, the charging process can be very slow and take more than 10 minutes to reach the 5 VDC threshold.

In the experiments, cases were examined where the input signal to the rectifying circuit was too small and a useful amount of power could not be conveyed to recharge the capacitor. In these cases, the bridge rectifier was substituted by a standard Villard multiplier circuit. To have a comparable result with those illustrated previously in this section, it was observed that when the multiplier is receiving a 11.8 V sinusoid in input (400 mV peak-to-peak signal from the USRP), the multiplier is able to generate a 20 VDC voltage as output. The time to completely recharge the capacitor is of about 600 s. In other words, the multiplier rectifies the AC signal and transforms part of the power into voltage producing a higher DC potential in output, but decreasing the current intensity. As a consequence, charging with a multiplier is more useful for low voltage inputs, but it can take longer periods of time to bring the internal charge of a storage component to the desired level.

Once the IMD (typically represented by a resistive load) requirements in terms of required power are known, one can evaluate the charge and the voltage drop across the supercapacitor that need to be reached. By using this voltage value in the curves in FIG. 5 and FIG. 6, and based on the input voltage to the system, one can predict how long it takes to charge the supercapacitor.

Also analyzed was the discharging behavior of the supercapacitor when, after being completely recharged, it was attached to a resistive load. Tracked were trends of voltage and current in time.

Figure 7:
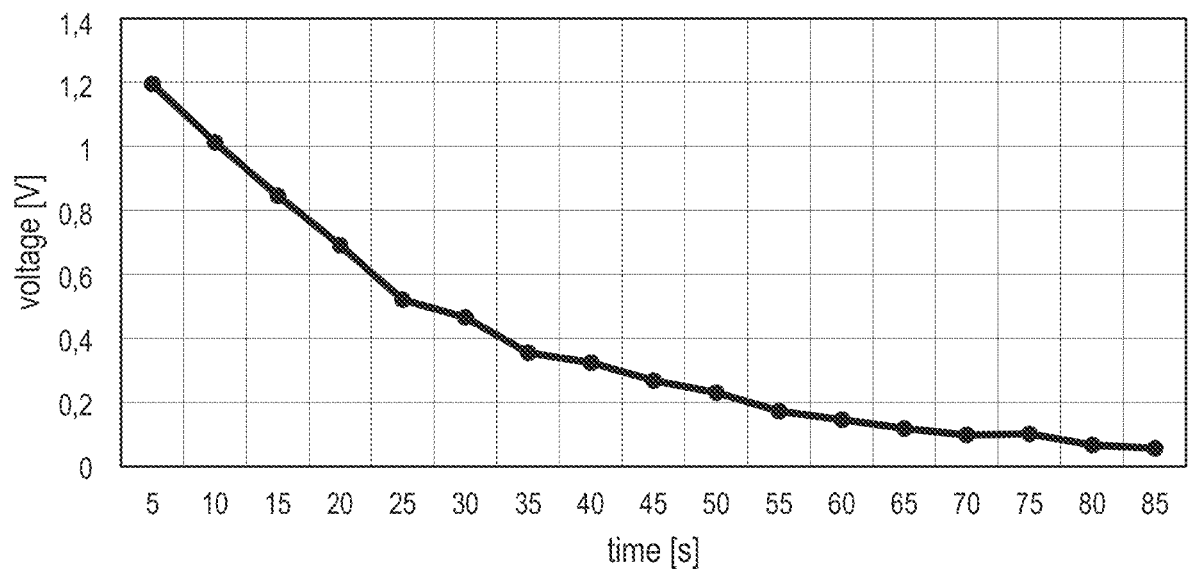
FIG. 7 is a graph illustrating supercapacitor voltage during a discharging phase with a 46Ω load.
Figure 8:
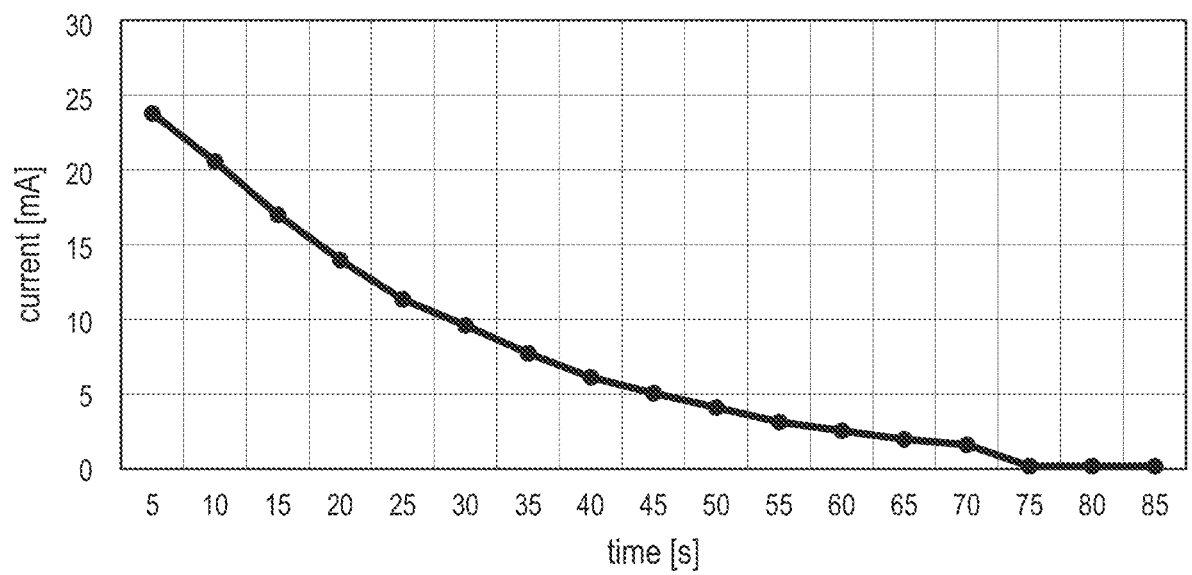
FIG. 8 is a graph illustrating supercapacitor current during the discharging phase with a 46Ω load.
Figure 9:
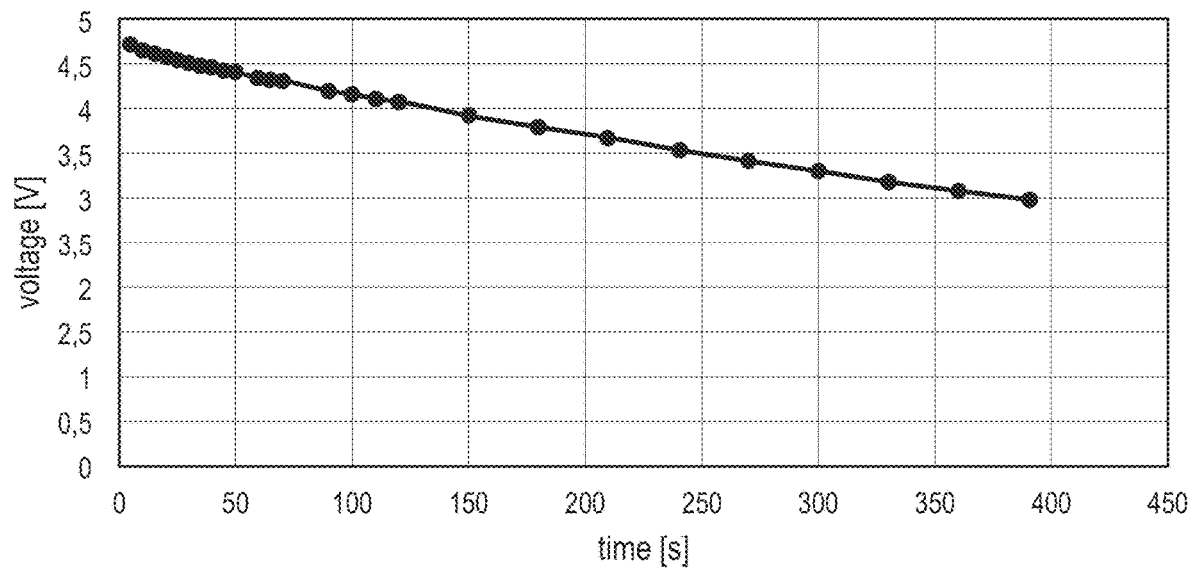
FIG. 9 is a graph illustrating supercapacitor voltage during a discharging phase with a 4.6 kΩ load.
Figure 10:
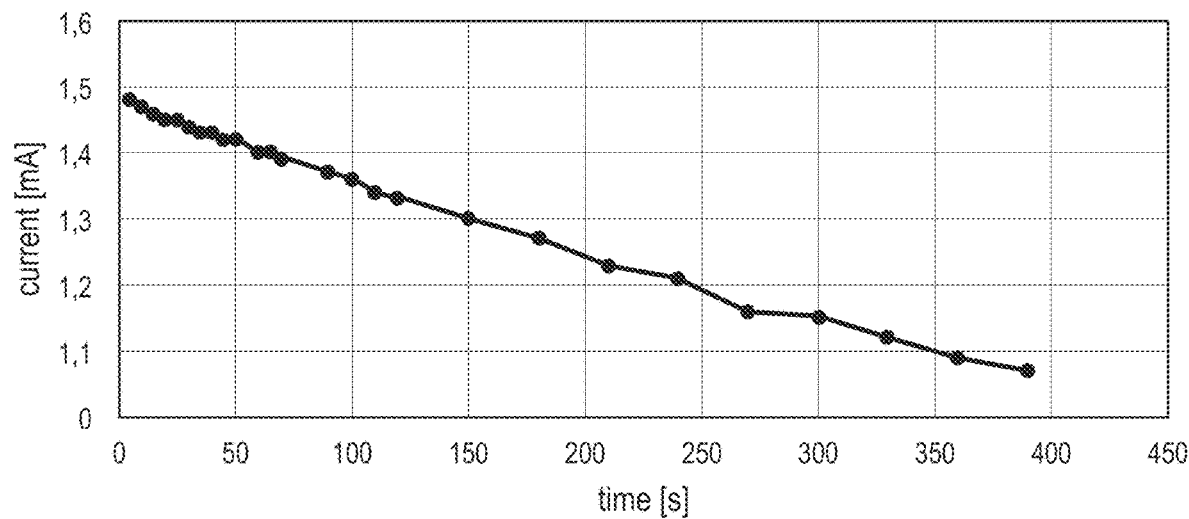
FIG. 10 is a graph illustrating supercapacitor current during the discharging phase with 4.6 kΩ load.

In FIGS. 7 and 8, the voltage across the supercapacitor and the current flowing into a 46Ω resistor, respectively, are reported. Analogous results are shown in FIG. 9 and FIG. 10, when the storage element powers a 4.6 kΩ passive load. Consistent with theory, given a certain time interval the lower resistance load absorbs more energy, while the higher, 4.6 kΩ load depletes the capacitor more slowly. In fact, in the first case (FIG. 8), the current goes to zero in about 80 s, while in the latter case (FIG. 10) the measured current values are still above 1 mA after 350 s.

VI. Analytical Model

The results reported in the previous Section are important, not only because they give an idea of the discharging times of the supercapacitor and of the load values that it is able to provide its energy to, but because they permit to build an analytical model to answer a fundamental question that can be stated as follows: Given an IMD and its requirements in terms of voltage, current, power, and time of operation (that is the time duration it has to be kept active), how long does it take to recharge the supercapacitor to a minimum level so that it is capable of offering the energy necessary to the implanted device?

This question can be answered by initially considering the plots of the voltage and current, such as in FIG. 7 and FIG. 8, or FIG. 9 and FIG. 10, corresponding to the load that has to be powered. For different load values not reported in the figures, similar curves can be derived from the test-bed. Once the operation time and the corresponding power required by the medical device are defined (time and power together providing the total energy), it is possible, by looking at the plots of the discharging phase, to evaluate the minimum voltage of the supercapacitor that has to be reached during the recharging interval. Finally, by entering the curves in FIG. 5 and FIG. 6 with the minimum values of the voltage and current previously obtained, and by choosing the appropriate curve corresponding to the USRP amplitude source signal, the time duration of the recharging phase can be determined and, consequently, the feasibility of the application at hand can be assessed.

REFERENCES

[A1] A. Toprak and O. Tigli, "Piezoelectric energy harvesting: State-of-the-art and challenges," Applied Physics Reviews, vol. 1, no. 3, p. 031104, 2014.
[A2] K. N. Bocan and E. Sejdic`, "Adaptive transcutaneous power transfer to implantable devices: A state of the art review," Sensors, vol. 16, no. 3, p. 393, 2016.
[A3] G. Santagati, T. Melodia, L. Galluccio, and S. Palazzo, "Medium access control and rate adaptation for ultrasonic intra-body sensor networks," IEEE/ACM Transactions on Networking, vol. 23, pp. 1121-1134, August 2015.
[A4] G. E. Santagati and T. Melodia, "U-wear: Software-defined ultrasonic networking for wearable devices," in Proceedings of the 13th Annual International Conference on Mobile Systems, Applications, and Services, pp. 241-256, ACM, 2015.
[A5] J.-Y. Tsai, K.-H. Huang, J.-R. Wang, S.-I. Liu, and P.-C. Li, "Ultrasonic wireless power and data communication for neural stimulation," in Ultrasonics Symposium (IUS), 2011 IEEE International, pp. 1052-1055, IEEE, 2011.
[A6] J. Charthad, M. Weber, T. C. Chang, M. Saadat, and Arbabian, "A mm-sized implantable device with ultrasonic energy transfer and rf data uplink for high-power applications," in Proc. of IEEE Custom Integrated Circuits Conference (CICC), e, pp. 1-4, September 2014.
[A7] R. Phillips and G. Harris, "Information for manufacturers seeking marketing clearance of diagnostic ultrasound systems and transducers," Food and Drug Administration, Center for Devices and Radiological Health, 2008.
[A8] E. Demirors, G. Alba, G. E. Santagati, and T. Melodia, "High Data Rate Ultrasonic Communications for Wireless Intra-Body Networks," in Proc. of IEEE Symposium on Local and Metropolitan Area Networks (LANMAN), (Rome, Italy), June 2016.
[A9] O. Shaul and S. Doron, "Non-invasive sensing of the electrical energy harvested by medical implants powered by an ultrasonic transcutaneous energy transfer link," in Industrial Electronics (ISIE), 2012 IEEE International Symposium on, pp. 1153-1157, IEEE, 2012.
[A10] https://www.americanpiezo.com.

EXEMPLIFICATION

U-CHARGE: Wirelessly Rechargeable Implantable Medical Devices with Ultrasonic Connectivity A variety of medical implantable devices (IMDs) are been developed in recent years that provide life-saving functionalities and enhance a patient's quality of life. One of the most challenging aspects faced by both traditional systems and futuristic designs is how to power or recharge the device under constraints on miniaturization while complying with low power levels allowed by the Food and Drug Administration (FDA). The next generation of implants will be endowed with wireless communication, sensing, processing and actuation capabilities, which increase the power requirements even more.

An ultrasonically powered miniaturized platform with wireless connectivity for medical applications is described. Design criteria and choices for each subsystem and component are presented, with particular attention to the power transfer efficiency (PTE). An example printed circuit board (PCB) for use in an implantable device is described. The example PCT is equipped with storage elements, power management circuitry, and ultrasonic communication technologies. In addition, experimental data resulting from testing the system is presented, showing that the energy harvested from ultrasonic waves can be used for sensing biomedical signals and communication purposes.

1—Introduction

Collaborative efforts between academic research, industry, and the medical community have produced a myriad of innovative implantable medical devices (IMDs), some of which are already commercially and clinically available today; while many more will be become available in the near future.

Cardiology.

Solutions in the field of heart pacing and implantable cardioverter-defibrillator (ICD) technologies during the last >50 years have helped sustain the lives of patients. In many cases, improvements in the quality of life and of the overall physical and psychological wellbeing of patients have been reported, as shown in multiple studies [12, 48]. However, the rate of sudden death in patients with cardiac implanted electronic devices (CIEDs) is still high and the physical and mental discomfort of wearing a pacemaker needs to be properly addressed [8]. A recent study [47] reported that 4.3% (22 of 217) of sudden deaths occurred in patients with a pacemaker or an ICD and half of them were caused by device failure or other issues. In addition, to date, several clinical demands, e.g., leadless and endocardial pacing, subcutaneous ICD, and sensing and monitoring of heart failure, among others, have not received a satisfactory solution yet [27].

Neurology.

Clinical medicine concerning neurological diseases has shown interest in wireless IMDs, for they have proved to be a proper answer to clinical signs and symptoms such as chronic pain, tremor, dystonia [46], blindness, deafness, epilepsy, and Parkinsonism [34]. Two main applications in this context are spinal cord stimulation (SCS) and deep brain stimulation (DBS). The first consists of a system including a pulse generator driving stimulating electrodes. The second, DBS, is realized by means of a brain pacemaker, a tiny device able to transmit electrical impulses to designated parts of the brain [46]. Miniaturization, long lifetime, and wireless networking capabilities are major requirements for a neurostimulator, but they are not completely met by existing and traditional devices.

Diabetes.

Diabetes Mellitus is one of the first causes of death and disability in the world. According to the World Health Organization, worldwide about 180 million people suffer from diabetes, a number that is destined to grow in the next years [6]. For instance, in the United States alone 8.3% of the population (25.8 million people) lives with diabetes, as reported by the Centers for Disease Control and Prevention [6]. It has been proved that the employment of miniaturized electronic microsystems will prevent type 1 and type 2 diabetes by monitoring the blood glucose concentrations and delivering appropriate amount of insulin [3].

From the considerations above, it follows that the IMD market is growing, driven mainly by the needs of the ever-aging population and the associated chronic degenerative diseases. In the U.S. alone, one million patients have CIEDs, and 250,000 pacemakers and 100,000 ICDs are implanted annually. Unfortunately, investments in early stages of innovation have seen a decline during the last years; conversely, financial support by investors is remarkable during the later stages of the development of a device. Nevertheless, the medical device industry remains in the fourth place as for investment volume with respect to other industrial sectors [30]. According to the Freedonia Group, the U.S. demand for medical implants is forecast to rise 5.1% annually to $53.2 billion in 2020 [16].

Technical Challenges.

Unique engineering challenges rise from the highly regulated market of IMDs [30]. In the U.S., the Food and Drug Administration (FDA) is the federal agency responsible for regulating medical devices. In the development process of millimeter (mm) and sub-mm sized electronic platforms, both safety and efficacy have to be approved by the FDA through non-clinical data, in order to enable clinical experiments in human subjects. This is a vital aspect, since implants can be defective [15] and lead to death in several cases [47].

The embedded electronic circuitry and subsystems require power, which, with biocompatibility issues, remains one of the major problematics in the design of implantable technologies and hindrance to miniaturization [6]. Implementing wireless powering methodologies that could substitute traditional batteries, is challenging, because both good energy transfer efficiency and high power levels are needed, but achieving them while meeting the FDA recommendations is one of the major difficulties. Furthermore, using miniaturized components impacts the system performance, since they determine the maximum sustained power, which in some cases is too low.

The advantages of providing an implantable platform with communication capabilities are undeniable, as they enable telemetry operations, intra-body networking, remote control and reprogramming of the implant itself. However, adding function to the system increases the overall energy requirements.

Features and Advantages.

Presented here is a transcutaneous energy transfer (TET) powered implantable platform with an ultrasonic feedback data link for assisting clinical applications. The platform includes, among others, the one or more of the following features and advantages:

A system includes an IMD equipped with ultrasonic communication capabilities and interfaced with a wearable power transmitter. The system is configured such that it uses ultrasound and utilizes the same piezoelectric transducers both for energy transfer and bio-telemetry.

Described are models of the system components and design choices of the subsystems, taking into account FDA power exposure limits and miniaturization aspects.

Presented are implementation aspects of a printed circuit board (PCB) relative to the realization of the implant on a miniaturized electronic chip.

Experimental results are presented that prove (i) the feasibility of wireless powering and (ii) that the harvested energy can drive the backward communication circuitry. Design of the system and evaluation of its performance are described, highlighting, in particular, the power transfer efficiency.

The remainder of the description is organized as follows. Section 2 describes the requirements, state-of-the-art, and details on technical challenges in the context of IMDs. In Section 4, the models of the system components and circuitry are explained. Section 5 illustrates the PCB details and shows the experimental results. Related work is presented in Section 7, followed by concluding remarks in Section 8.

2—Preliminary Considerations

This section sets forth requirements of the most common IMDs, in terms of power required for their operation, physical constraints in the miniaturization process, and communication capabilities for intra-body communication. Some of the existing solutions are briefly described.

2.1—Requirements and State-of-the-Art

Powering.

IMDs are, depending on the application, more or less complex platforms encompassing various subsystems, e.g., transducers, power management unit and energy storage, data communication and processing units, sensing and actuating units.

The amount of power required by medical implants depends on the technology at hand and it can span from the order of microwatts to a few watts. A modern neurostimulator needs from 0.42 mW up to 100 mW. Progress in the CIEDs industry has reduced the power needs, producing more power-efficient devices. In 2010, a pacemaker needed about 100 mW; nowadays, there are systems that work with 1-8 [22, 44]. An ICD absorbs higher levels of power ranging from few hundreds of micro-watts in steady state to 5-10 W to generate a shock [1, 41]. Endoscopy and gastrointestinal capsules are among the most power greedy devices, because of the combined functions they perform, including motion, sensing, and actuation. About 220-800 mW is the power to move the capsule around; other actuators need more than 200 mW. The remaining subsystems (LEDs, image sensors, communication unit) of the capsule absorb up to 40 mW each [10, 38]. In contrast, glucose sensors can operate with voltage values as low as 200 mV [3].

There exist essentially three possibilities when it comes to powering these electronic bio-implants, and they are described below [1, 24].

Batteries and Supercapacitors.

Batteries are the technology commonly employed today and they have been widely used in commercial products. On the one hand, batteries can offer enough energy to power an IMD, such as a pacemaker, for years; on the other, they pose three fundamental concerns that limit their applicability to IMDs. Batteries are often too large in size, the materials used in their fabrication can be toxic for human tissues in case of leakages and, finally, once discharged, they have to be substituted through a surgical operation that entails economical costs, discomfort, and even death risk for the patient.

An alternative to batteries is offered by supercapacitors. Unlike standard ceramic capacitors, supercapacitors do not have a dielectric between the plates (electrodes). Instead, an electrolyte is filled between them, resulting in a high capacitance value. While batteries have higher energy density, supercapacitors have better power density and are smaller. Moreover, supercapacitors can be recharged more easily and faster than batteries, and virtually an infinite amount of times. Micro- and thin film supercapacitors have also been proposed that can be appealing substitutes for batteries [4].

Energy Harvesting.

Energy harvesting is the idea of collecting energy from the environment surrounding the device and converting it into electrical energy by means of a transducer [37]. The literature is very rich in designs, prototypes, and studies specific for medical implants [7, 18]. In these works, the harvesting methodologies have been be classified based on the physical principle of energy conversion that they adopt and/or the nature of the energy source exploited. The main difficulties in creating an implantable harvester are related to the technology to fabricate the transducer and to the nature of the source. For example, microelectromechanical systems (MEMS) and piezoelectric transducers scavenge kinetic energy mainly from human body motion (which is a discontinuous source, and therefore unreliable in many cases) and autonomous organ activities, such as breathing and heartbeat, that instead do not provide the necessary required power. Electrostatic and electromagnetic (EM) converters are mechanically complex systems, which makes the miniaturization a challenging process. Other solutions, e.g., solar and optical harvesters [32], and thermoelectric generators [2, 50], and applicability only to more superficial (subcutaneous) implementations.

Transcutaneous energy transfer (TET). While the two previous approaches fall in the category of independent implants, a TET (or wireless power transfer—WPT) system requires an external transmitter that exploits wave propagation phenomena to deliver power to the receiver on the implant side. The presence of the external transmitter adds complexity to the whole system, but has the advantage of creating a continuous, reliable, and controllable energy source. Furthermore, higher transmitted power levels can be reached. In fact, most harvesters can only generate power values of the order of microwatts, while an order of magnitude higher can be achieved with systems with an external unit [18, 34]. There are several physical principles that can be exploited to realize a remote powered IMD [1]. Capacitive coupling [20], inductive coupling [23, 28, 31], and high radiofrequency (RF) coupling [5, 40] are all energy transmission mechanisms based on the propagation of EM fields. However, acoustic and ultrasonic TET (UTET) technologies [9, 36, 46] are a valid substitute and the solution opted for in the present work. Ultrasound in the human body has also been long used for medical imaging.

Hybrid Strategies.

Hybrid alternatives are also possible. A battery powered system can take advantage of a rechargeable supercapacitor to reduce the size of the battery and benefit from the advantages of a remote rechargeable system. After all, in the majority of both energy harvesting based approaches and TET solutions, the energy cannot be used the moment it is received or harvested. Hence, an energy storage component is needed; this can be in the form a rechargeable battery or a supercapacitor.

Miniaturization.

The design of a medical device structure needs to take into account not only strictly engineering aspects, but also scientific, biological, and medical constraints. Therefore, if an electronic circuitry implements the sensing, communication and data processing properly, but is too large or does not respect the power exposure limits, it cannot be implanted. Consequently, substitute chip and components have to be found or the concept has to be reworked [21].

Numerous efforts have been made in order to engineer miniaturized components suitable for IMDs [13]. Most of these are in the area of energy storage components [4], inductor coils, and RF antennas [25, 26], as they represent the bulkiest elements of the implant.

The design of an implantable platform is also application dependent and its dimensioning is constrained by the specific body part or organ where it will be implanted. To have a reference of the physical size of a medical implant, a few examples are considered. An intracranial pressure monitor should be small enough to fit in standard 12 mm burr holes in the skull [26]. Endoscopy capsules have to be swallowable, so their typical size is 11 mm×25 mm [38]. The Micra transcatheter pacing system, claimed to be the world's smallest pacemaker, is self-contained in a capsule that can be inserted in the heart ventricle. It is 25.9 mm long with a diameter of 6.7 mm, and a total volume of 0.8 $cm^3$.

Less restrictive, in terms of dimensions, is the layout of the external data/power transceiver unit, but ergonomics is generally a good criterion to keep in mind. Furthermore, particular miniaturized solutions have to be found for wearable or patch-like devices thought to be attached to the skin.

Wireless Communication for IMDs.

Equipping a miniaturized board with a wireless transceiver unit has several advantages to the system. Communication capabilities enable medical telemetry that is measuring of biological parameters and physiological signals and sending them from the implant to an external receiver. The link can also be used in the opposite direction, that is, to send data from outside of the body to the IMD, in order to reprogram or reconfigure it. In the large picture of Internet of Medical Things (IoMT) [42], implantable sensor nodes and actuators can be wirelessly connected, not only with wearable devices, but also with each other in a so called intra-body network and work synergistically by exchanging data sensed in different parts of the body. In addition, a communication unit also allows the IMD to send alerts and status updates to an Internet-connected device and, from here, directly to a physician [12].

TET systems with a data transfer link have been discussed in some literature studies. In one report [35], an ultrasonic WPT scheme with a backward data link is illustrated. The data link is realized by varying the impedance of the receiver that, in this way, reflects part of the energy then used to transfer information back. Changing the reflection coefficient reduces the harvested power by 19% when a '1' bit is transmitted. Other implementations use two different vehicles to transfer energy and data, e.g., electromagnetic induction and ultrasounds. Other approaches deal with energy transfer and data communication in human body separately. Some relevant approaches are discussed in Section 7 below, while the technical considerations on building a miniaturized remote powered system, including a wireless data feedback channel, are explored in Section 4.

3—System Design

Working Under FDA Limitations.

The most common wireless methods used today for data transmission are based on RF communication, while contactless charging mainly exploits low frequency inductive coupling. However, a promising alternative that has been extensively investigated, both for data and energy transmission, is offered by ultrasonic waves. The FDA sets the exposure limits of the human body to the different kinds of radiated power that can have hazardous effects if above certain thresholds. In particular, 720 mW/cm$^2$ is the maximum allowed power superficial density in tissues for acoustic waves, while 10 mW/cm$^2$ is the EM radiation limit. These safety limitations translate into design constraints and impact the dimensioning of the whole system.

Here is a basic difference between contactless energy transfer and wireless telecommunication. In data transferring, the received power level can be very low, as far as the transmitted power is high enough to distinguish the signal from the noise. Instead, in WPT, achieving higher efficiency and transmitting more power is essential to convey enough energy to the storage components with sufficient charges [46].

The opportunity of transmitting more power, together with the smaller attenuation in human tissues as compared to EM waves [11, 42], is the reason for the use of ultrasound in the present system.

Power Transfer Efficiency (PTE).

Figure 11:
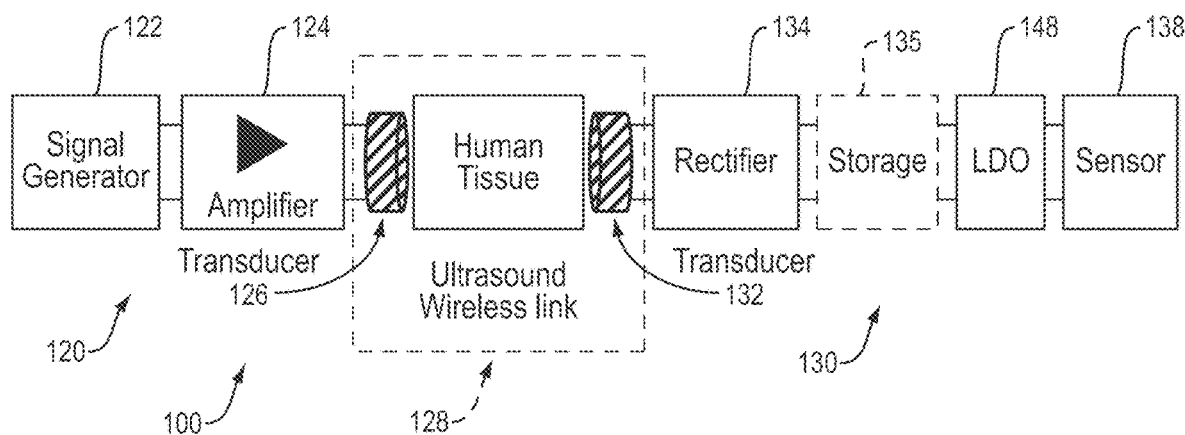
FIG. 11 is a block diagram of an Ultrasonic Transcutaneous Energy Transfer (UTET) system according to an example embodiment of the invention.

Based on the system described above with reference to FIG. 1 and the report in [17], a high level description of a basic UTET system is provided. FIG. 11 depicts a block diagram of a generic ultrasonic wireless recharging system 100. The objective of the system structure is to deliver enough power to an energy storage installed on the implantable platform 130 from a charging device 120, positionable outside the body, by means of ultrasonic propagation via a wireless link 128.

A periodic signal, that can be a sinusoid or a square wave, is generated at ultrasonic frequencies (>20 kHz) by a signal generator 122 to drive, via amplifier 124, an electro-acoustic transducer 126. The transducer 126 converts the electric signal to ultrasounds. Acoustic waves are essentially mechanical waves, and as such, they need a medium to propagate. In this case, the medium is represented by the human body itself. The interface between the human skin and the piezoelectric surface (and more precisely the packaging containing the transducer) introduces a mechanical impedance mismatch, while the tissue between the transmitter and the receiver attenuates the wave propagating through it. At the receiving side (implanted device 130), an acoustoelectric converter (transducer 132) transforms the mechanical excitation back into an electrical alternating current (AC) signal. The power management unit, in its most basic form, contains a rectifier circuit 134 and a low dropout (LDO) regulator 148 to limit the voltage delivered to the load, which can be a sensing or actuation unit 138 (a medical device including, e.g., a sensor, an actuator, a drug pump, a heart stimulator, etc.). An energy storage 135 need not be present. In some applications, the received power is directly transferred to the load. The energy storage, if present, typically needs a direct current (DC) voltage in order to be recharged, which explains the presence of the rectifier whose role is to generate a DC voltage from an oscillating input.

A low dropout (LDO) regulator is a DC linear voltage regulator that can regulate the output voltage even when the supply voltage is very close to the output voltage. Advantages of a LDO voltage regulator over other DC to DC regulators include the absence of switching noise (as no switching takes place), smaller device size (as neither large inductors nor transformers are needed), and greater design simplicity (usually consists of a reference, an amplifier, and a pass element).

The sensing and/or actuating unit 135 can employ a variety of sensors to sense biological parameters or actuators to actuate biological or medical procedures.

In embodiments, a sensor can comprise a motion sensor, a gyroscope, an accelerometer, a cardiac rhythm monitor, a heart rate monitor, a pulse monitor, a blood pressure sensor, a glucose sensor, a drug pump monitor, a sleep sensor, a REM sleep duration sensor, an optical sensor, a still camera, a video camera, a sensor for one or more biomolecules, a sensor for one or more pharmaceutical agents or pharmaceutical formulation ingredients, a sensor for a dissolved gas or ion, or a sensor for pH, ionic strength or osmolality.

In embodiments, the actuator can comprise a drug pump, a heart stimulator, a heart pacemaker, a deep brain stimulator, a neurostimulator, or a neuromuscular electrical stimulator.

Each stage of the energy delivery path illustrated in FIG. 11 introduces losses that have to be accounted for by efficiency parameters. The total efficiency, from the output of the external power generator to the energy storage, or the IMD can be decomposed as, $$\eta_{tot} = \eta_{tx} \times \eta_{e2a} \times \eta_{tissue} \times \eta_{a2e} \times \eta_{rect} \quad (1)$$

where $\eta_{tx}$, $\eta_{tissue}$, and $\eta_{rect}$ are the power transfer efficiency from the source to the transmitting transducer, the efficiency through the human tissue, and the rectifying efficiency, respectively. In each of the two conversion process, part of the input power is lost due to non-idealities of the devices. Thus $\eta_{e2a}$ and $\eta_{a2e}$ account for the "electrical-to-acoustic" and the "acoustic-to-electrical" conversion efficiencies of the transmitting and receiving transducers, respectively. The ultrasonic link 128 comprises the two transducers (126, 132) and the medium in between; therefore, the power transfer efficiency (PTE) of the wireless link can be defined as the percentage in (2) [31]:

$$\eta(\%) = \frac{P_{Rx}}{P_{Tx}} \times 100 \quad (2)$$

(with $P_{Tx}$ being the power transmitted by the transducer and $P_{Rx}$ the received power) and decomposed as the product in (3):

$$\eta_{link} = \eta_{e2a} \times \eta_{tissue} \times \eta_{a2e} \quad (3)$$

Architectural Model.

Starting from the schematic diagram in FIG. 11, a system for wireless ultrasonic recharging with the addition of a data communication unit can be provided.

Figure 12:
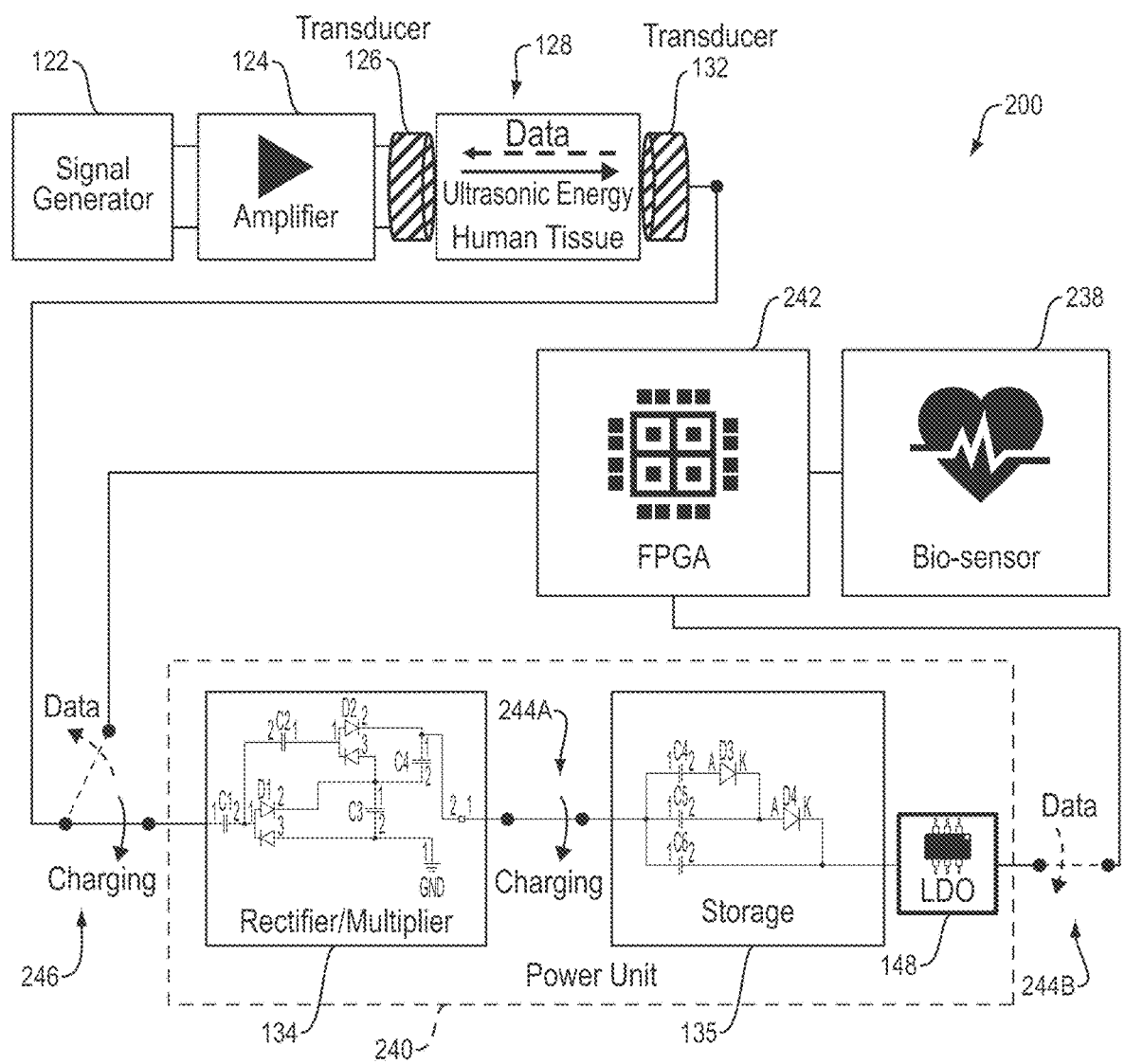
FIG. 12 is a block diagram of a UTET system including a power unit, programmable circuitry, and a biosensor.

The architectural model of the system is illustrated in FIG. 12. Besides the blocks in FIG. 11, the system includes a processing unit, e.g., a field programmable gate array (FPGA) 242, a sensor for medical applications 238, specifically a pressure sensor, and switches 246, 244A, and 244B to pass from charging mode to data transmission mode, and vice versa.

The FPGA 242, which can be substituted by a microcontroller unit (MCU) in some applications, implements the ultrasonic transceiver to enable communication data processing operations. The sensor 238 passively scans biological signals, such as the heartbeat, and sends the data to the FPGA 242. In the illustrated design, piezoelectric transducers (PZTs) are used for transducers 126 and 132. The system operation can be conceptually divided into two different phases. During the initial charging phase, the circuit behaves basically as described before with reference to the structure in FIG. 11. Once enough energy has been stored, the switches are activated so that the data transferring phase can start. The switch 244A connects the rectifier/multiplier 124 and the storage 135, while the switch 244B connects the storage 135 to the FPGA 242, which is receiving data from the sensor 238. Although shown as two switches 244A and 244B, the same functionality can be achieved using a single switch, such as illustrated by switch 44 in FIG. 2. The switch 246, which during the charging phase links the transducer 132 (in receiving mode) with the rectifier/multiplier 134, changes the operation modality of the implanted device from powering to data transmission mode. In fact, when the switch 246 is positioned on "data," output of the FPGA 242 drives the transducer 132 that transmits the data through the body.

4—System Modeling

This section describes the mathematical models, formal characterization, and operational details of the sub-systems and devices that realize the general architecture defined in Section 3. Design procedures are also highlighted.

4.1 Characterization of the Piezoelectric Transducers

In the design of an ultrasonic link that adopts piezoelectric-based transducers, both their mechanical and electrical behaviors should be taken into account.

Propagation Effects.

Geometrical factors and operating frequency impact the propagation characteristics of the ultrasonic radiation. The beam spread angle of a PZT with a circular radiating surface decreases with the diameter of the transducer and the operating frequency, as implied by (4) (see [14]):

$$\sin\left(\frac{\alpha}{2}\right) = \frac{0.514v}{fD} \quad (4)$$

where $\alpha$ is the beam spread angle from the central axis at −6 dB, v is the propagation speed of acoustic waves in the medium, f is the frequency of radiation, and D the diameter of the transducer. The term "$\alpha/2$" is called beam divergence angle.

By substituting numerical values in equation (4) one can find the spread angle $\alpha$ of the transducers used in the system. Table 1 lists the fundamental parameters of the ultrasonic link adopted in the implementation described in Section 5. Substitution of these values in equation (4) gives the maximum and minimum beam spread angles: $\alpha(600\text{ kHz})=18.2°$ and $\alpha(800\text{ kHz})=13.6°$ (see FIG. 21).

TABLE 1

| Ultrasonic link parameters | |
| --- | --- |
| Parameter | Value |
| Transduce diameter | D = 9.5 mm |
| Sound speed in tissues | v = 1500 m/s |
| Operating frequency | f = 600-800 kHz |
| Distance | d = 50 mm |

Figure 13:
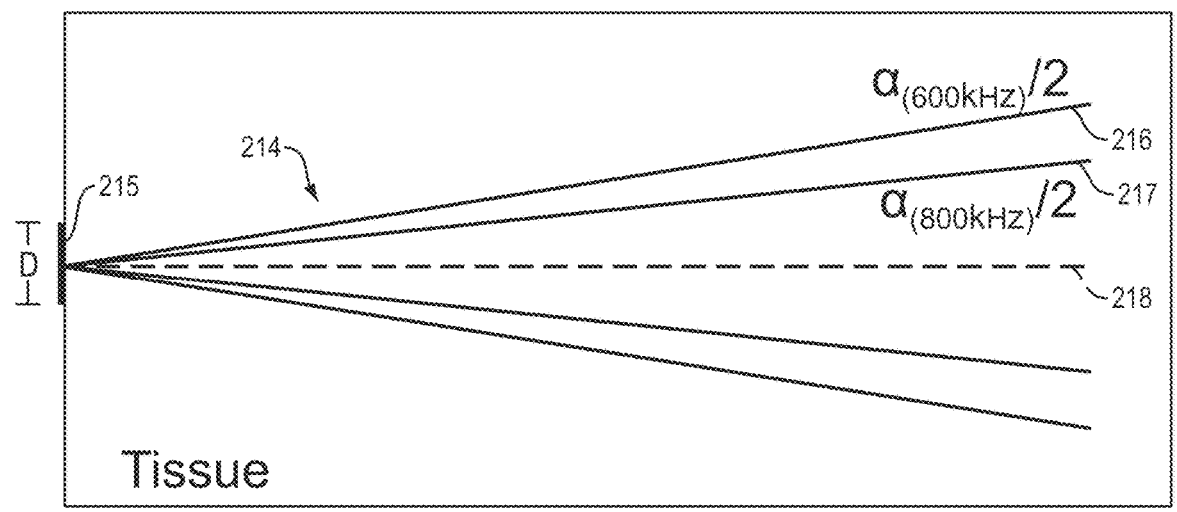
FIG. 13 illustrates beam spreading of a piezoelectric transducer (dimensions are in scale).

FIG. 13 schematically illustrates the beam spreading effect of a D=9.5 mm transducer 215 and the same parameters as provided in Table 1. The figure shows the maximum 216 and minimum 217 beam spread angles, as described above. The beam 214 is rather narrow, especially at short distances of few centimeters from the surface of the PZT, which introduces the problem of the geometrical misalignment between transmitting and receiving PZT. In fact, as also highlighted in [43], in order to maximize received power and efficiency, the on-skin transmitter and the implanted PZT should be as much aligned as possible on the same central axis 218.

Conversion Efficiency.

As formalized in (1), a transducer is characterized by electro-acoustic and acoustoelectric conversion efficiencies. While the radiation pattern of a PZT is reciprocal, i.e., the directivity is the same whether the device is used in transmission or reception operating mode [14], the same cannot be said for the conversion efficiency. It is of interest to measure the electro-acoustic efficiency of the device used in this system, firstly because it is easier to maximize the efficiency intervening on the transmitting side by tuning the wave generator on the resonating frequency, and secondly, because increasing the efficiency during the wireless powering phase is more critical than during the data transmission phase.

TABLE 2

| Measurement circuit parameters | |
| --- | --- |
| Parameter | Value |
| Power amplifier ZHL-6A + gain | 24.81 dB |
| Pre-amplifier Teledyne Reson VP2000 gain | 50 dB |
| Source signal | 2 V (peak-to-peak) |
| Distance between transducers | d = 1 m |

The sound power level $P_{SPL}$, or acoustic power level, measures the power of a sound at a nominal distance of 1 m, expressed in dB relative to a reference value $P_0=1$ pW:

$$P_{SPL} = 10\log_{10}\left(\frac{P_S}{P_0}\right)(\text{dB}) \quad (5)$$

$P_{SPL}$ is also equal to $$P_{SPL} = P_{RPL} + 10\log_{10}\left(\frac{A_S}{A_0}\right) \quad (6)$$

where $P_{RPL}$ is the received power level, measured in dB, $A_S$ is a surface that wholly encompasses the source, and $A_0=1$ m$^2$ is a reference surface. Equation (7) relates the received power level $P_{RPL}$ to the sound pressure U $$U = 10^{P_{RPL}/20} \text{ (µPa)} \quad (7)$$

U is function of the root mean square (RMS) value of the received voltage $V_{RMS\text{-}rx}$ through M:

$$U = V_{RMS\text{-}rx}/M \ (\mu Pa) \quad (8)$$

and M is given by:

$$M = 10^{RVS/20} \ (V/\mu Pa) \quad (9)$$

One can calculate the sound power $P_S$ (in W) by inverting the relation in (5) and expressing $P_{SPL}$ as in (6).

$$P_S = 10^{\left[P_{RPL} + 10\log_{10}\left(\frac{A_S}{A_0}\right)\right]/10} \cdot P_0(W) \quad (10)$$

Figure 14:
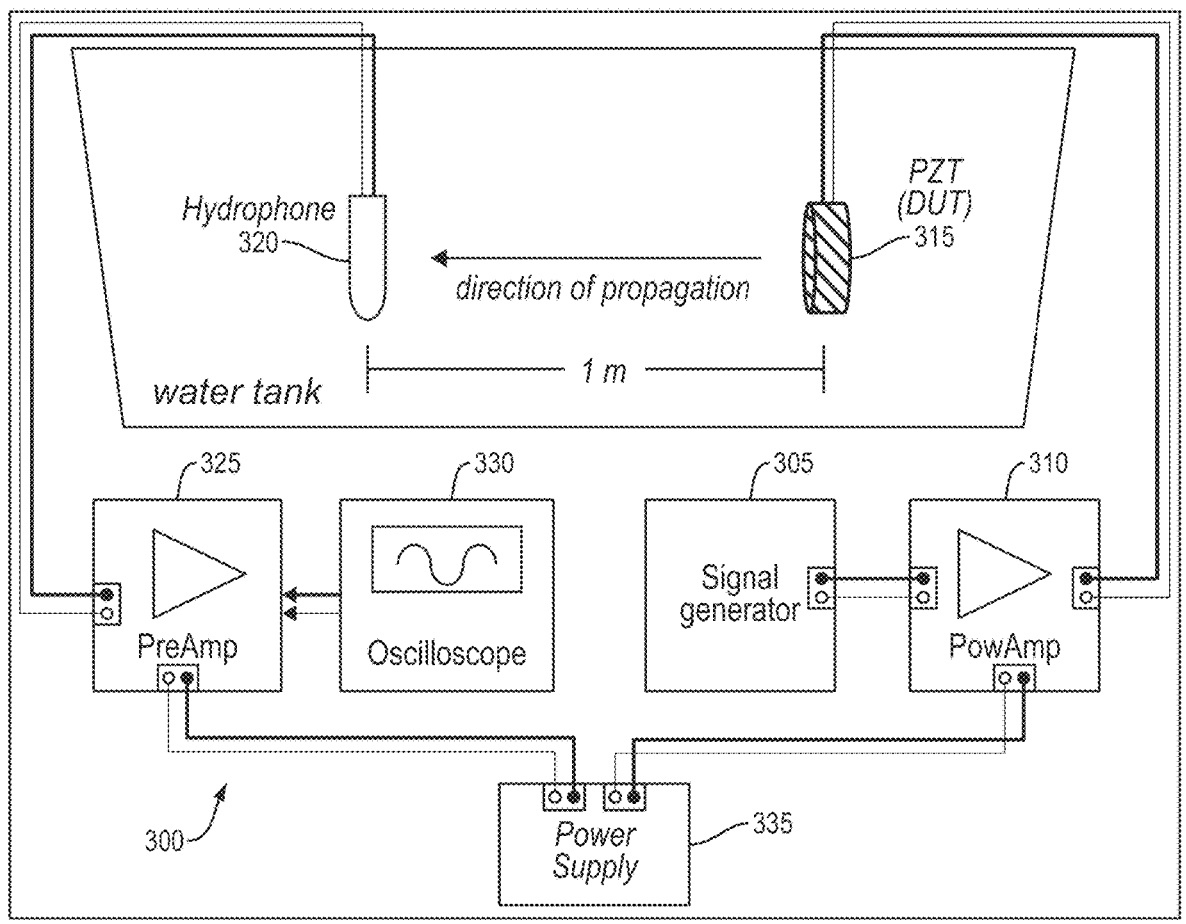
FIG. 14 illustrates a measurement system to evaluate piezoelectric transducer conversion efficiency.

To evaluate the PZT conversion efficiency, a measurement circuit 300, illustrated in FIG. 14, was set up with the values listed in Table 2

To conduct the experiments, a signal generator 305 is used to produce a sinusoid. The signal is amplified by a Mini Circuits ZHL-6A+ amplifier 310 that, in turn, drives the PZT 315—device under test (DUT)—immersed in a tank filled with water. The ultrasounds propagate through the water and are received by a hydrophone 320, e.g., Teledyne Reson TC4038 hydrophone, located at the distance of 1 m. The received waveform is pre-amplified by means of an amplifier 325, e.g., a Teledyne Reson VP2000 amplifier, before being measured by a standard oscilloscope 330. A power supply 335 powers the amplifiers 310, 325 and can power any of the other devices coupled to the amplifiers.

Figure 15:
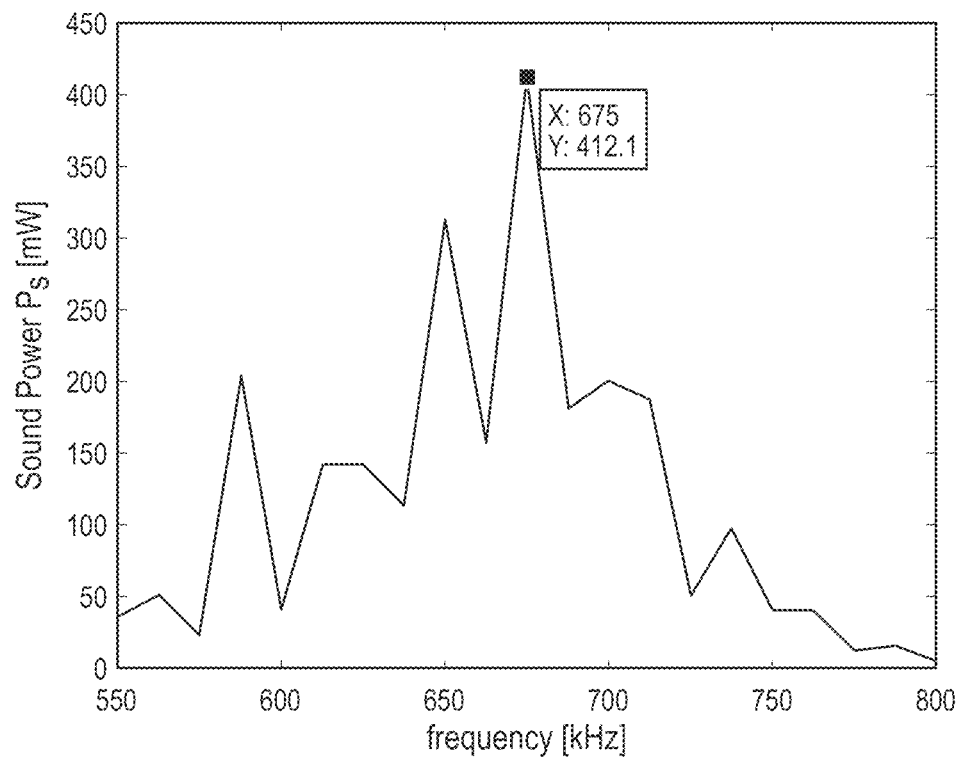
FIG. 15 is a graph illustrating sound power emitted by an example ultrasonic transducer as a function of frequency.
Figure 16:
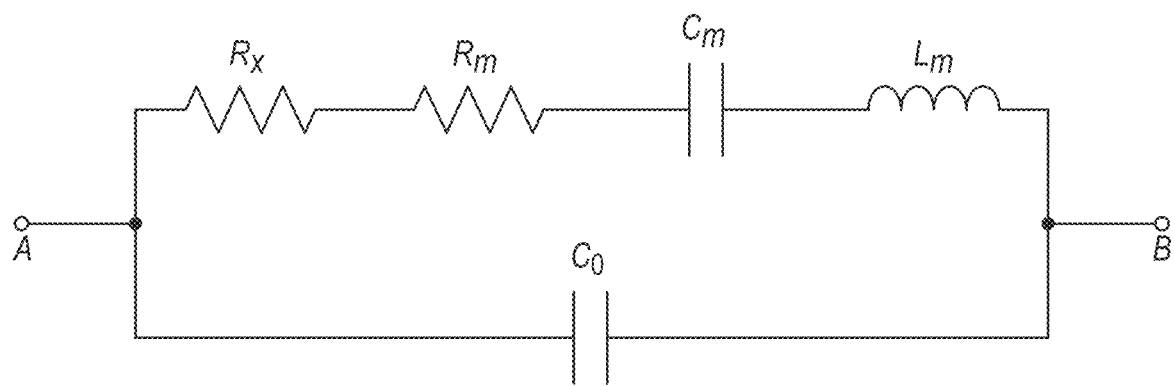
FIG. 16 is a circuit diagram of a piezoelectric transducer Butterworth-Van Dyke equivalent model.

Calculations were carried out on the basis of the formula discussed above. The plot in FIG. 15 represents the measured sound power PS as function of the frequency. Even though the nominal central frequency of the PZT is 700 kHz, the best performance can be reached at 675 kHz; the device has a bandwidth of about 200 kHz. These results are confirmed by the measurements reported below for the electrical characterization. This range of frequencies is a good compromise between attenuation of ultrasonic waves in human tissues (increasing with frequency), and radiation directivity (increasing with frequency as well). The PZT diameter of 9.5 mm is a trade-off between size (so that it can be implantable) and conversion loss (that increases with reduced diameter) and directionality (increases with smaller sizes) [42].

Electrical Characterization.

From an electrical point of view, a piezoelectric transducer behaves like a high capacitive load and it can be modeled as a Butterworth-Van Dyke circuit (refer to FIG. 6) [45]. The electrical behavior is described by $C_0$ and $R_x$, where the first is the clamping capacitor and the latter accounts for the electrical losses. Instead, $C_m$, $L_m$, and $R_m$ are representative of the mechanics of the device.

Figure 17:
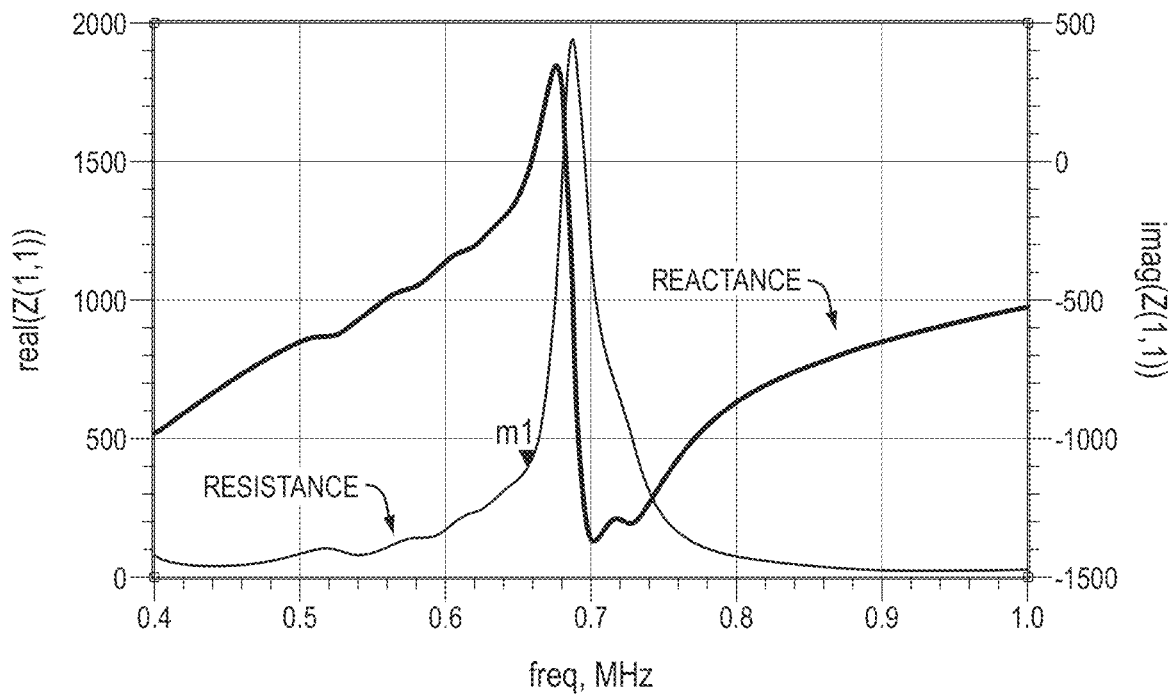
FIG. 17 illustrates resistance and reactance of an example piezoelectric transducer.

The impedance of the PZT can also be measured using a network analyzer calibrated on a purely resistive 50Ω load. FIG. 17 illustrates measured resistance (real part of the impedance Z) and reactance (imaginary part of Z) of an example piezoelectric transducer.

4.2—Transmitter Power Amplifier

Striving to reach the maximum transmissible power allowed by the FDA (720 mW/cm²) is preferred, especially during the recharging phase. Transmitting at higher power levels, meeting the FDA regulation, has several benefits, e.g., recharging time intervals can be shorter, wireless powering becomes applicable to deep implants (>5 cm), more charges are accumulated, and higher voltage are available, at the storage components. Typically, the signal produced by the signal generator needs to be amplified before driving the piezoelectric converter. To this end, an amplifier in combination with a transformer can be used [45]. When choosing the amplifier, an important parameter to take into account is the gain-bandwidth product (GBW). The GBW expresses the product of the open-loop voltage gain $A_{ov}$ and the frequency f at which it is measured, and is given by (11):

$$GBW = A_{ov} \times f \quad (11)$$

Figure 18:
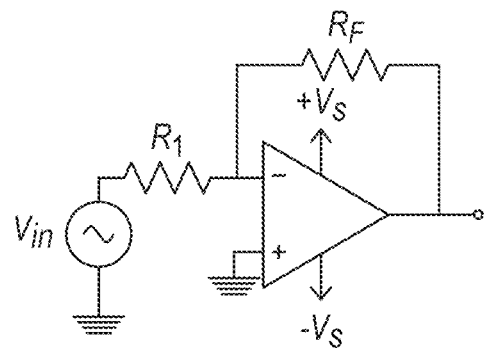
FIG. 18 is a circuit diagram of an Op-Amp in inverting configuration (supply ±VS).

GBW is constant for voltage-feedback amplifiers and it determines the maximum gain that can be extracted from an amplifier at a specific frequency. Conversely, if the amplifier is configured to work at a specified gain GBW, it will amplify signals up to a certain frequency (bandwidth) f A main goal of the remote charging phase is to transfer energy; hence, an operational amplifier (Op-Amp) in a basic inverting configuration can be used. FIG. 18 shows an Op-Amp in a traditional inverting configuration useful for a wearable transmitter.

With reference to FIG. 18, the open-loop voltage gain is given by $A_{ov} = V_{out}/V_{in} = -R_F/R_1$. This means that by appropriately choosing the resistors $R_F$ and $R_1$, the gain $A_{ov}$ can be optimized. However, given the product in (11) and defined the operating frequency of the circuit, it is straightforward to determine the maximum amplification value of the inverting configuration.

4.3—Rectifier Circuits

Figure 19:
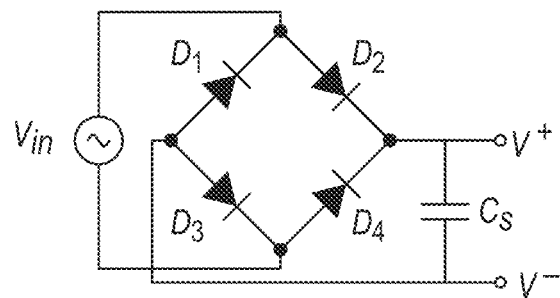
FIG. 19 is circuit diagram of an example full wave rectifier.

Full wave diode rectifier. As explained in Section 3, a UTET system calls for a rectifying circuit to extract a DC energy source from the received AC signal, in order to provide a continuous voltage to the storage and recharge it. One of the simplest passive AC-to-DC power conversion circuits is the full bridge rectifier (see FIG. 19) that consists of four diodes and one smoothing capacitor $C_s$.

The available average rectified voltage across a load placed between V+ and V− is:

$$V_{dc} = V^+ - V^- = \frac{2 \cdot V_{pk}}{\pi} \quad (12)$$

and its RMS value is $V_{RMS} = V_{pk}\sqrt{2}$, where $V_{pk}$ is the amplitude (peak) of the AC input signal. The approximate ripple factor of a diode bridge rectifier is expressed as $F = 1/(fR_L C_s)$, where f is the frequency and $R_L$ the load resistance. The conventional efficiency of the rectifier is the ratio between the output DC power and the input power supplied to the circuit; it is calculated with (13):

$$\eta_{rect} = \frac{P_{dc}}{P_{ac}} = \frac{V_{dc}^2/R_L}{V_{RMS}^2/R_l} = 0.812 = 81.2\% \quad (13)$$

Multiplier Circuit.

Figure 20:
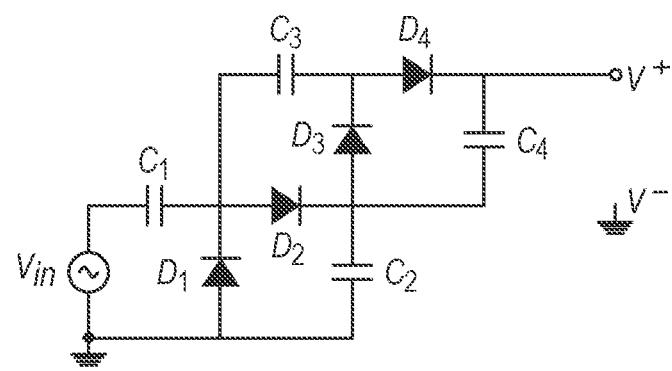
FIG. 20 is a circuit diagram of a traditional Cockroft-Walton cascade multiplier.

An alternative to the rectifier is presented by a traditional multiple stage multiplier circuit. The schematic of a traditional 2-stage Cockroft-Walton quadrupler is illustrated in FIG. 20. The advantage of this circuit is twofold. On the one hand it rectifies the AC input, on the other, the output open circuit DC voltage is about n times the input voltage $V_{pk}$, where n is the number of stages (doublers) that the circuit implements. The disadvantages are the higher number of capacitors and the lower current at the output. However, having larger DC voltages is desirable in low-power circuits, because they allow recharging an energy storage component even when the received AC voltage is of the order of few hundreds of milliwatts and would not provide enough power with a rectifier.

The number of stages n is a fundamental design parameter, but a trade-off needs to be found. The output voltage is directly proportional to n, however there is a limit on the maximum number of stages that can be used, as the conversion efficiency of the circuit is function of n. Higher voltages can be produced in output by increasing n, but the conversion efficiency decreases due to power loss caused by parasitic effects of the capacitors [33]. Moreover, increasing the number of stages also implies that more components need to be accommodated on the implant, occupying precious area on the board. The voltage ripple $V_r$ affecting the rectified waveform in the Cockroft-Walton multiplier is given by (14):

$$V_r = \frac{I}{fC} \frac{4n^3 + 3n^2 - n}{3} \tag{14}$$

where I is the current flowing through the load, f the operating frequency, and C the capacity of $C_i$, $1 \leq i \leq 4$.

4.4 Storage

Traditionally, a chemical battery has energy but not power while the capacitor has power but not energy. This relationship is now undergoing rapid transformation. A key relationship is that the energy on a capacitor in joules is proportional to half the capacitance (in farads) times the voltage squared: Energy (joules)=½×Capacitance (Farads)× Voltage². Either a high number of Farads or a high voltage increases the energy storage of a capacitor significantly.

4.5—FPGA-Based Communication Unit

Application-specific integrated circuits (ASICs) provide an optimized hardware solution for signal processing and networking functions. ASICs are designed and permanently configured only for one specific application; hence, they do not provide the flexibility and reconfigurability required in many cases. Furthermore, design and fabrication of such systems are highly expensive and time consuming. Field-programmable gate arrays (FPGAs) are innovative computing devices merging the benefits of both hardware and software. They are characterized by low power consumption, optimized area efficiency. Computations can be spatially redistributed and millions of operations can be performed simultaneously by resources embedded on the chip. Similar to software implementations, FPGAs provide fast and cheap reprogrammability, and they are faster than microprocessor-based systems. However, FPGAs performance can be from 5 to 25 times worse than ASIC implementations, and operations more complex to define with respect to microprocessor [19]. In contrast to ASICs, in which the computations are permanently imprinted during the fabrication process, FPGAs can be reprogrammed multiple times, even during operation. The reasons for reprogramming the device vary and include adding new features, setting it up for a new task. Based on these considerations, it is desirable to embed an FPGA in the architecture of the system, as shown in FIG. 12, to equip the implantable device with data processing and an ultrasonic backward link for communication.

5—Implementation and Evaluation

This section describes the layout of a PCB implementing the architecture illustrated in Section 2 (FIG. 12). The basic electrical components are chosen considering the design concepts and formula of Section 4. In some cases, similar devices are compared via simulation or experimental evaluation. Finally, performance results relative the entire ultrasonic system, and tests of parts of the PCB are presented and discussed.

5.1—PCB Description and Technical Details

The PCB was designed using off-the-shelf electrical components and the most important are listed in Table 3. The choice of some devices, e.g., supercapacitors, was in sometimes not optimal, especially when it cannot be found off-the-shelf material that meets the values calculated during the design phase.

Paying careful attention to the size of each subsystem, one can select elements that keep the overall volume of the device contained. This is often a trade-off between size and power (or current) absorption. Table 4 summarizes the dimensions of the circuits and devices composing the example PCB.

TABLE 3

PCB components details

| Circuit | Component | Value/Model | # |
|---|---|---|---|
| Rectifier | Diode | BAT-54A | 2 |
|  | Smoothing capacitor | 0.01 µf | 1 |
| Multiplier | Diode | BAT-54S | 2 |
|  | Capacitor | 0.01 µF | 4 |
| Storage circuit (1) | 2-input prioritizer | LTC4419 | 1 |
|  | Supercapacitor | 100 mF (ESR 25Ω) | 1 |
|  | Supercapacitor | 47 mF (ESR 30Ω) | 1 |
| Storage circuit (2) | 2-input prioritizer | LTC4419 | 2 |
|  | Supercapacitor | 300 mF (ESR 75Ω) | 1 |
|  | Supercapacitor | 47 mF (ESR 30Ω) | 2 |
| Voltage regulator | LDO | TPS727 | 1 |
| Control | Timer | ST TS555 | 1 |

The choice of the diodes adopted in the rectifier and multiplier is based on simulation results. BAT-54x and 1N4148 diodes have similar performance, thus SPICE preventive simulations helped establish that BAT-54A/S were the best choice for the proposed AC-to-DC circuits. The smoothing capacitance depends on the load resistance, but in this project, the load is ideally purely capacitive. In reality, some parasite resistances, non-ideal behavior of the components, and the ESRs of the supercapacitors add up to a small resistive load. For this reason, a relatively small smoothing capacitor can be used, which was selected experimentally before fabricating the PCB.

TABLE 4

PCB circuits and components dimensions

| Circuit/component | Size |
|---|---|
| Rectifier | 7.0 mm × 3.7 mm |
| Multiplier | 9.5 mm × 5.0 mm |
| Storage circuit (1) * | 10.0 mm × 6.2 mm |
| Storage circuit (2) * | 20.0 mm × 13.0 mm |
| Supercap. Panasonic (330 mF) | 10.5 mm × 6.5 mm ** |
| Supercap. Kemet FC (100 mF) | 10.5 mm × 5.5 mm ** |
| Supercap. Elna DVN (47 mF) | 12.5 mm × 8.5 mm ** |
| Voltage regulation and LDO | 8.4 mm × 4.2 mm |
| Timer ST TS555 | 6.0 mm × 4.9 mm |

* Storage component not included
** diameter × thickness

Figure 21:
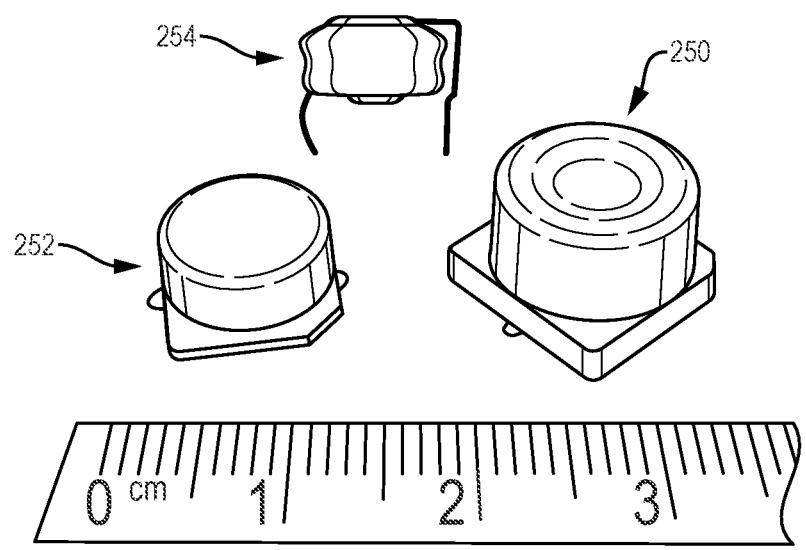
FIG. 21 illustrates example supercapacitors that can be used in embodiments of the invention.

In order to test the PCB for a range of applications, it is equipped with two storage circuits, comprising one larger supercapacitor 250 and one or two smaller supercapacitors 252, 254 (FIG. 21). For details of the components see Table 3 and Table 4.

The smaller capacities are intended for back-up operations, or providing an extra charge in case the main storage depletes, or for emergency. The main and the back-up supercapacitors are connected so that they are charged in parallel and discharged in sequence. The three LTC4419 dual input micropower prioritizers are used to select which supercapacitor the energy should be drawn from. The choice of these storage components resulted from an analysis and balance of capacity, relative ESR, form factor, and size. In real scenario applications, only one of the two storage circuits may be realized, and different capacity values can be calculated if needed.

The board can also be used for direct powering, which implies that all the storage can be completely removed, as also discussed in Section 3, and the rectified voltage directly applied to a load. The experiments to evaluate the efficiency are based on this idea. The efficiency cannot be measured as defined in (13) when the load is capacitive, because the circuit is in transient phase and not in steady state. In this case, a time-dependent absorbed power, and consequently $P_{dc}$, has to be considered. Many clinical applications require some form of control; therefore, it is useful to embed a timer, e.g. the ST TS555 timer, on the board. The timer can be used to control an intermittent powering, for example, in a heart pacing scenario.

5.2—Experimental Results

Figure 22:
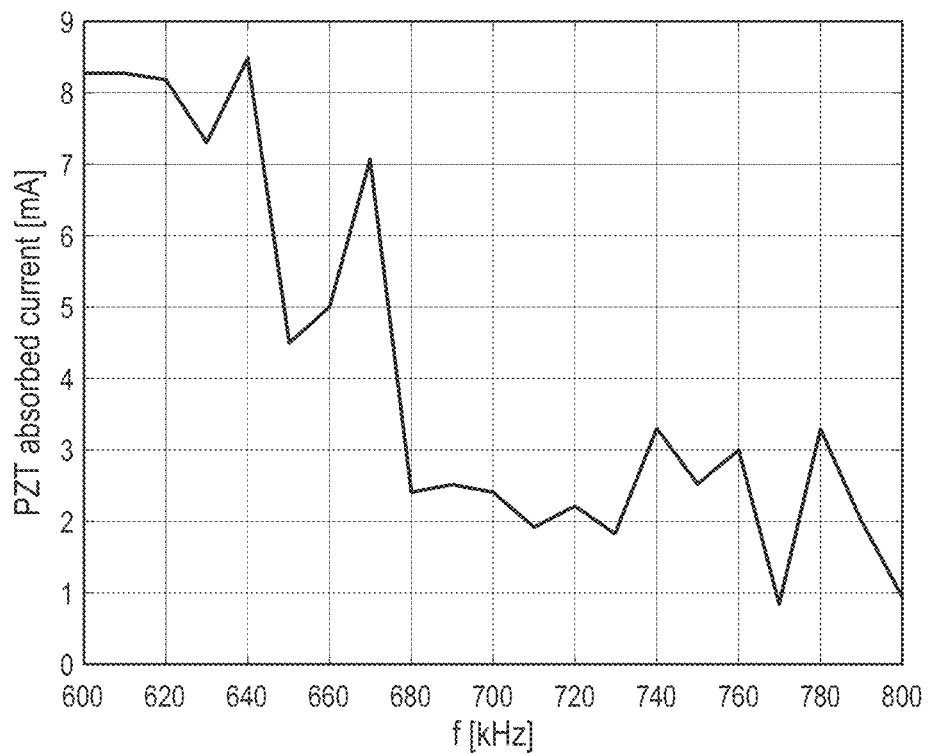
FIG. 22 is a graph illustrating current absorbed by a piezo-electric transducer (PZT) as a function of frequency.
Figure 23:
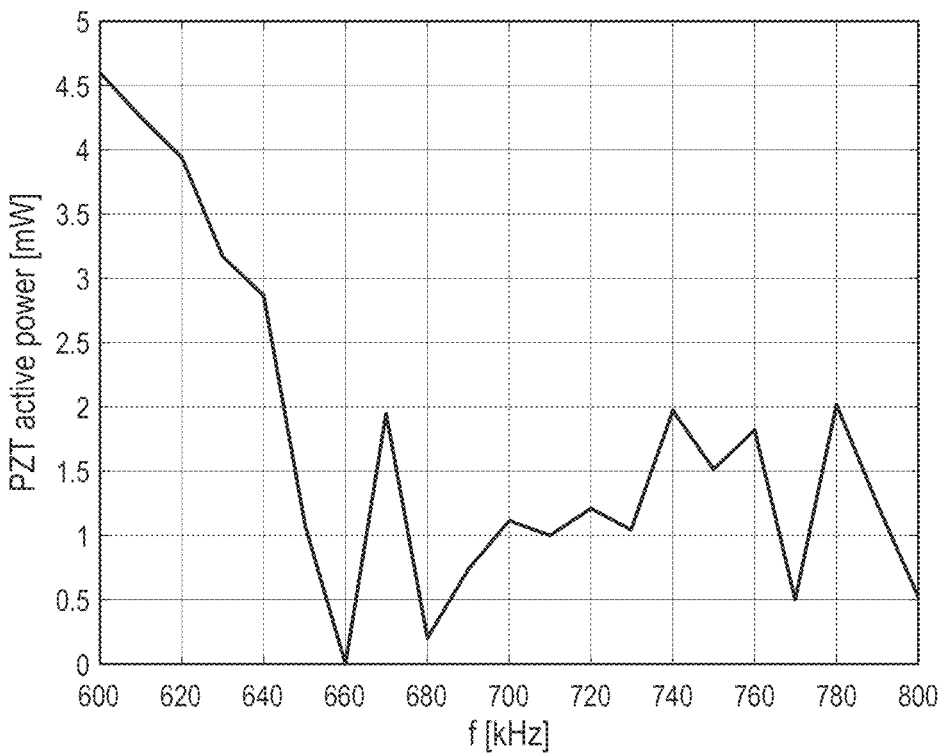
FIG. 23 is a graph illustrating power absorbed by the PZT as a function of frequency.
Figure 24:
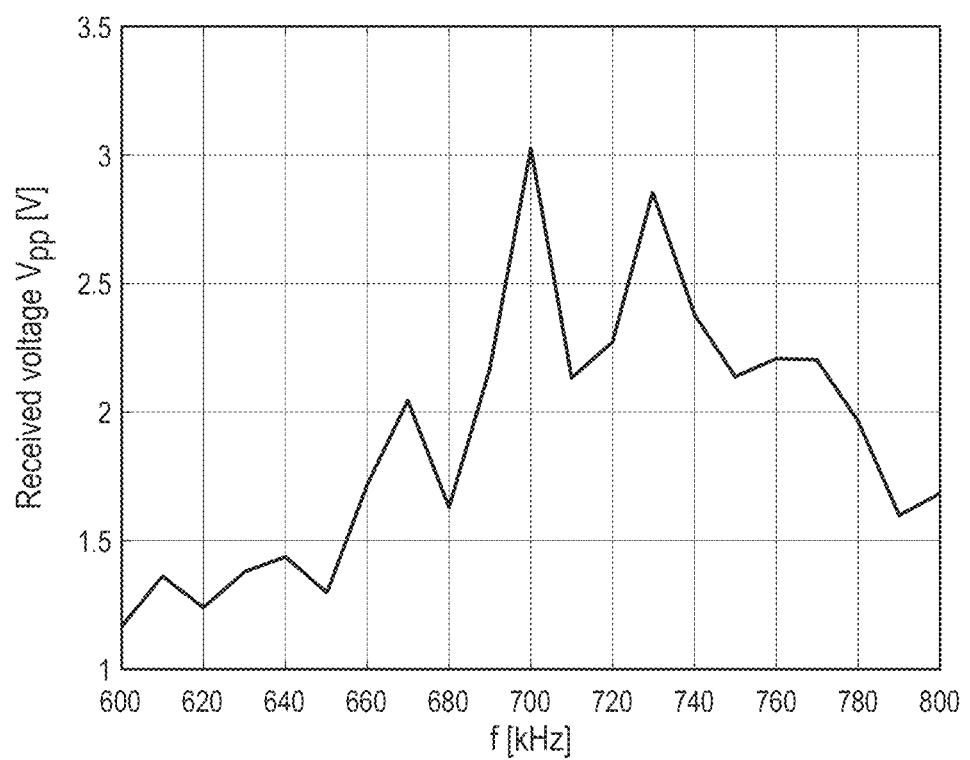
FIG. 24 is a graph illustrating received peak-to-peak voltage as a function of frequency.

In all the experiments, human tissue was emulated by means of a synthetic upper arm phantom that has the same mechanical properties of human muscle tissue containing veins and blood. The transducers are placed on the sides of the phantom at 5 cm from each other. A water-based, acoustic adaptation gel is used to match the ultrasonic impedance and reduce the losses. A first set of experiments allowed measurement of the current (FIG. 22) and power (FIG. 23) absorbed by the transmitting piezoelectric converter for different values of the frequency and a fixed 5 V peak-to-peak transmitted voltage. Despite the sensitivity peak value seen at 675 kHz (FIG. 15), the highest received voltage was measured at 700 kHz, as shown in FIG. 24.

Figure 25:
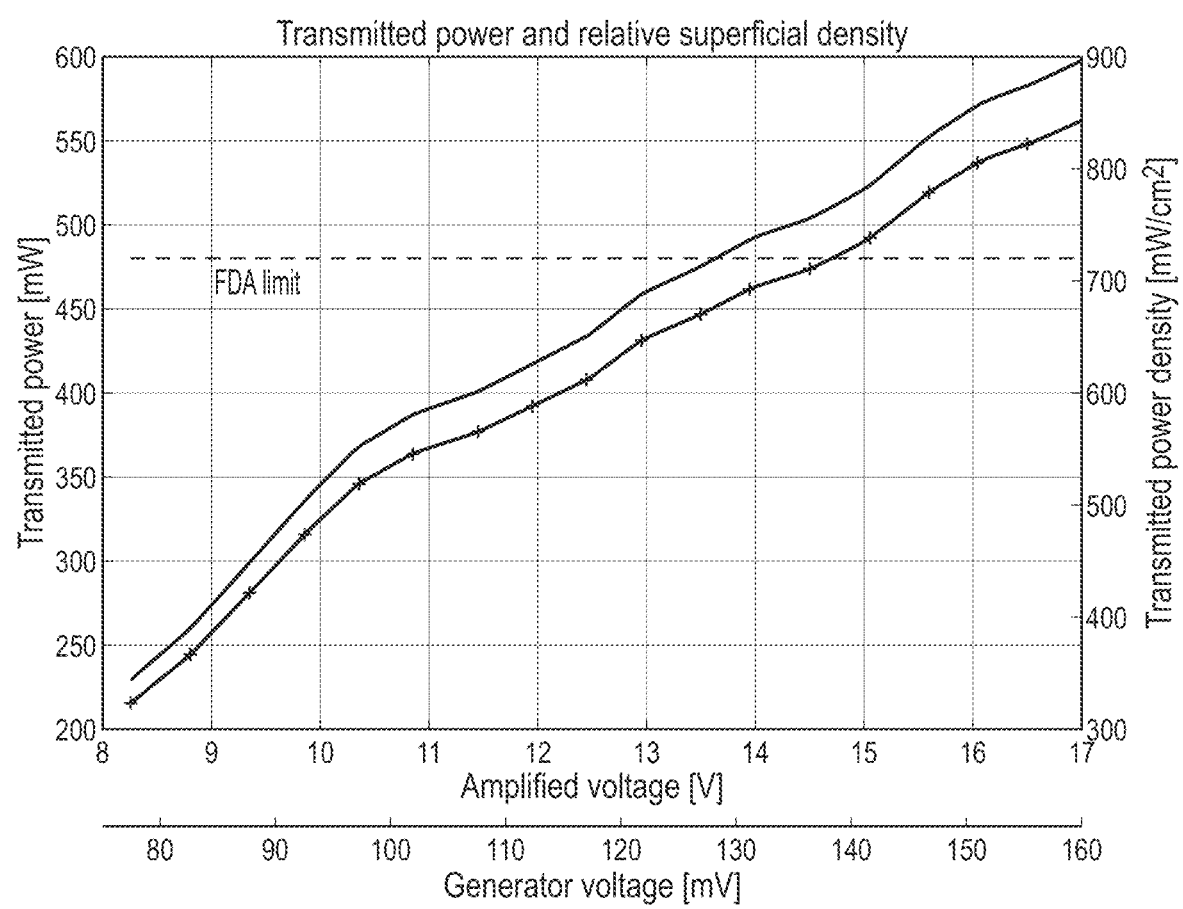
FIG. 25 is graph illustrating transmitted power (solid line without marker) and power density (solid line with "+" marker).

It is important to measure the power driving the transmitting PZT to be sure that the system is compliant with the FDA limits. If the transducer had an ideal energy conversion of 100% and was perfectly matched to the generator's load, given its surface of $\pi(D/2)^2=0.71$ cm$^2$, the maximum transmittable power would be 511 mW, which leads to a superficial power density exactly equal to the FDA exposure limit. The active power delivered to the transducer is given by $P_a = V_{rms} I_{rms} \cos \varphi$, where $V_{rms}$ and $I_{rms}$ are the RMS values of the AC voltage and current, and $\varphi$ the phase between the voltage and current waveforms. The curves in FIG. 25 show the transmitted power and the corresponding superficial power density for a range of input voltage values close to the FDA limit at the frequency of 700 kHz. The intersection of the transmitted power density with the horizontal threshold defines the maximum voltage to use to drive the PZT, and 14.5 V is the voltage amplitude applied to the transducer in the experiments.

The performance of a miniaturized power amplifier is analyzed, specifically an AD825 amplifier. This amplifier is appealing for wearable applications, given its small size of 5 mm×6 mm×2 mm. The GBW of this chip is 26 MHz, meaning that at 700 kHz the gain is equal to G=37. The saturation of the amplifier allows input AC voltages up to few hundreds of millivolts of amplitude. Consequently, the AC voltage received after propagation through the tissue is less than 3 V and able to recharge only half of the storage up to 2.5 V. The amplification gain can be increased by creating a multi-stage amplification circuit or adopting a bootstrapping technique.

Figure 26:
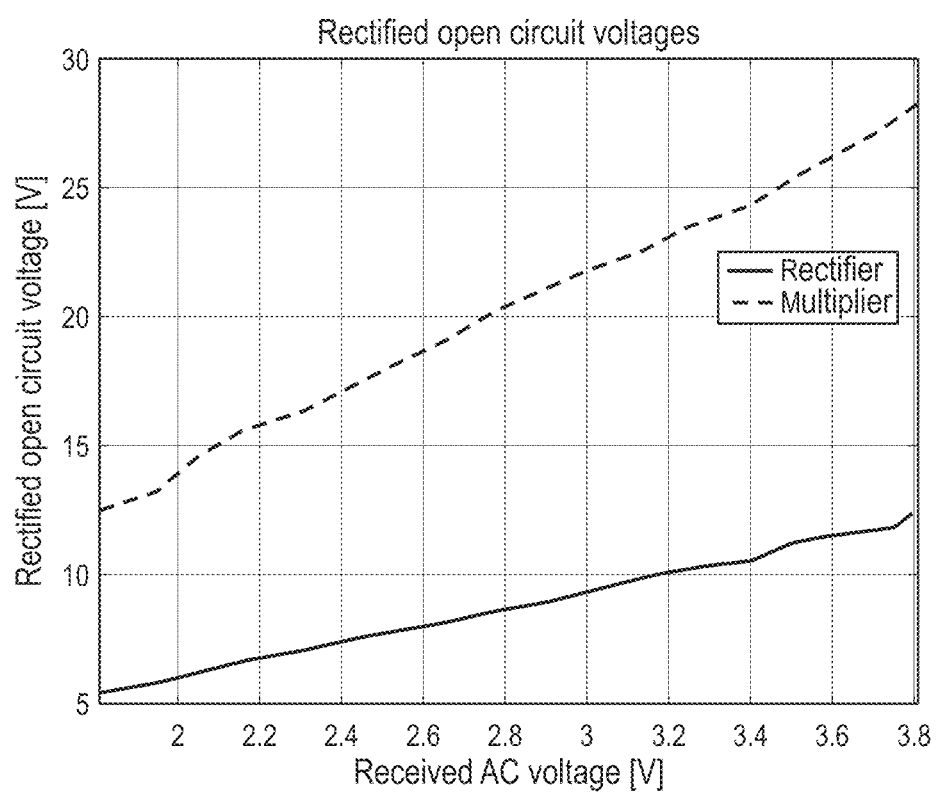
FIG. 26 is a graph illustrating rectified open circuit voltages using a rectifier (solid line) and a multiplier (dashed line).
Figure 27:
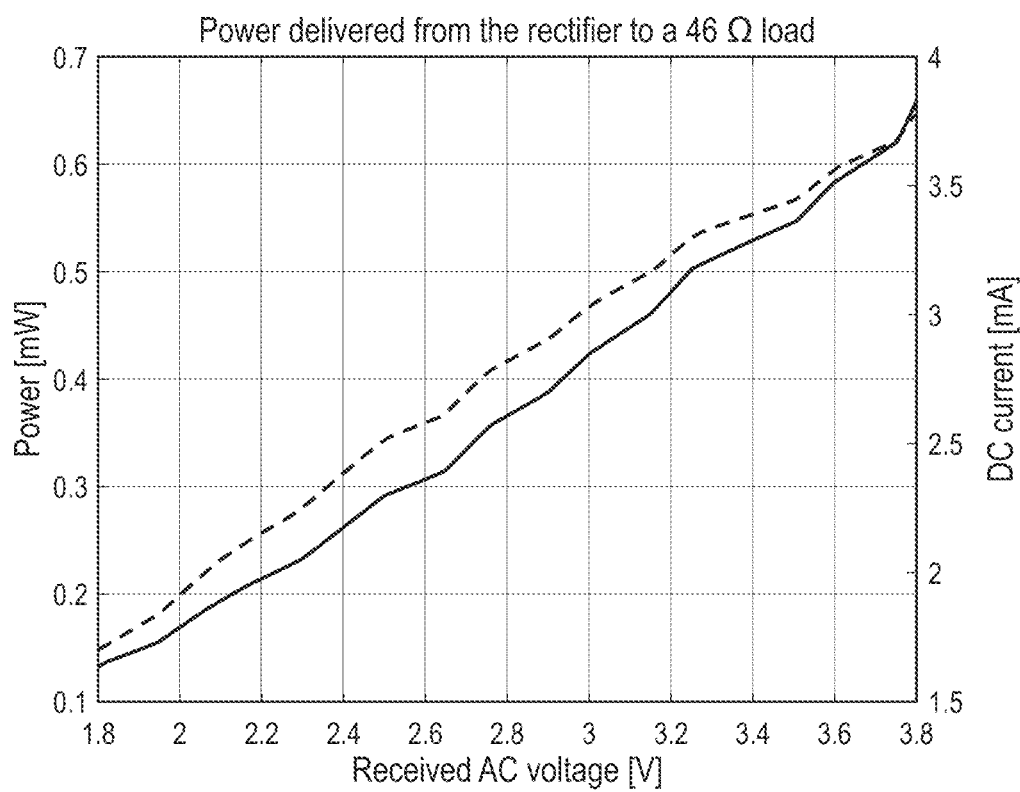
FIG. 27 is a graph illustrating power (solid line) and DC current (dashed line) delivered to a 46Ω load from the rectifier.
Figure 28:
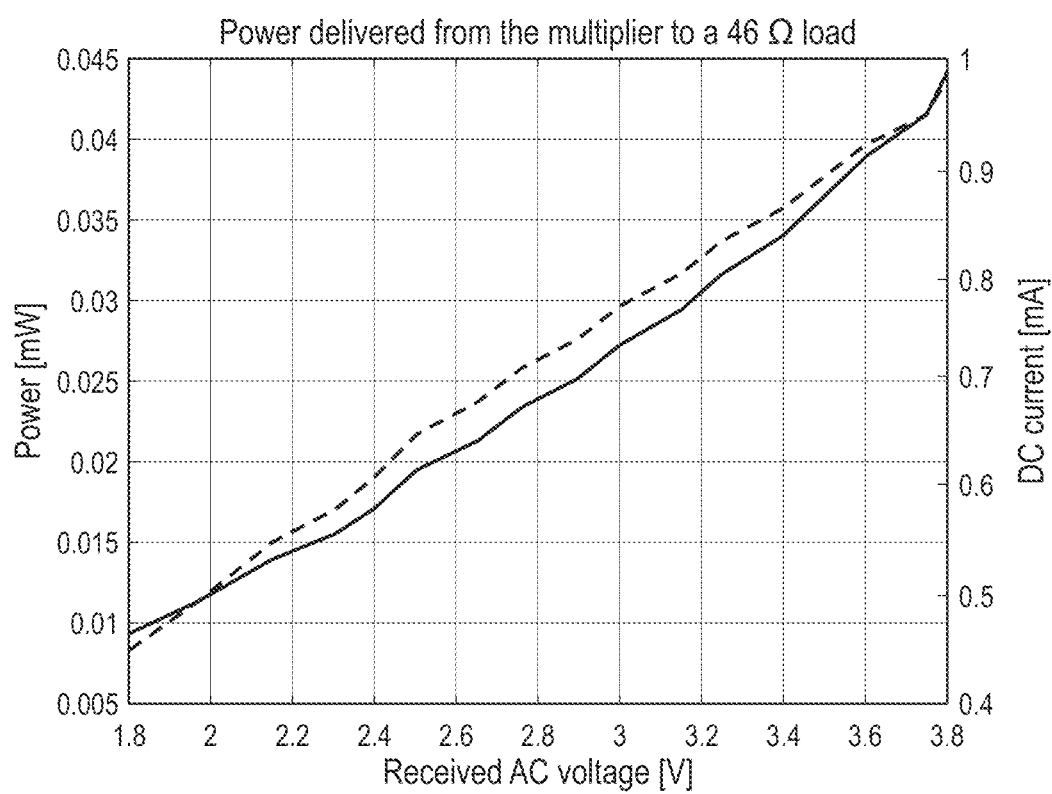
FIG. 28 is graph illustrating power (solid line) and DC current (dashed line) delivered to a 46Ω load from the multiplier.

The results of a comparison of the rectifier and the multiplier, carried out through a series of measurements, can be observed in FIGS. 26 to 28. FIG. 26 is a graph illustrating rectified open circuit voltages using the rectifier and the multiplier. FIGS. 27 and 28 are graphs illustrating power and DC current delivered to a 46Ω load from the rectifier and the multiplier, respectively. Even though the voltage extracted by the multiplier is higher than the rectified DC voltage, the latter circuit is more effective. The reason for this difference can be understood by inspecting the rectified current and power that the two circuits are able to deliver to a reference load.

A reference load of 46Ω was chosen, as this value is close to the typical equivalent series resistance (ESR) of the supercapacitors. In this way it is possible to have an idea of the initial power that the circuits can transfer to the storage systems. From FIG. 27 and FIG. 28 it is clear that the output current available at the multiplier is of the order of tens of milliwatts, while in the rectifier case, it is of one order of magnitude higher. The explanation can be found in the fact that the multiplier uses part of the power (current) to generate a higher voltage.

Figure 29:
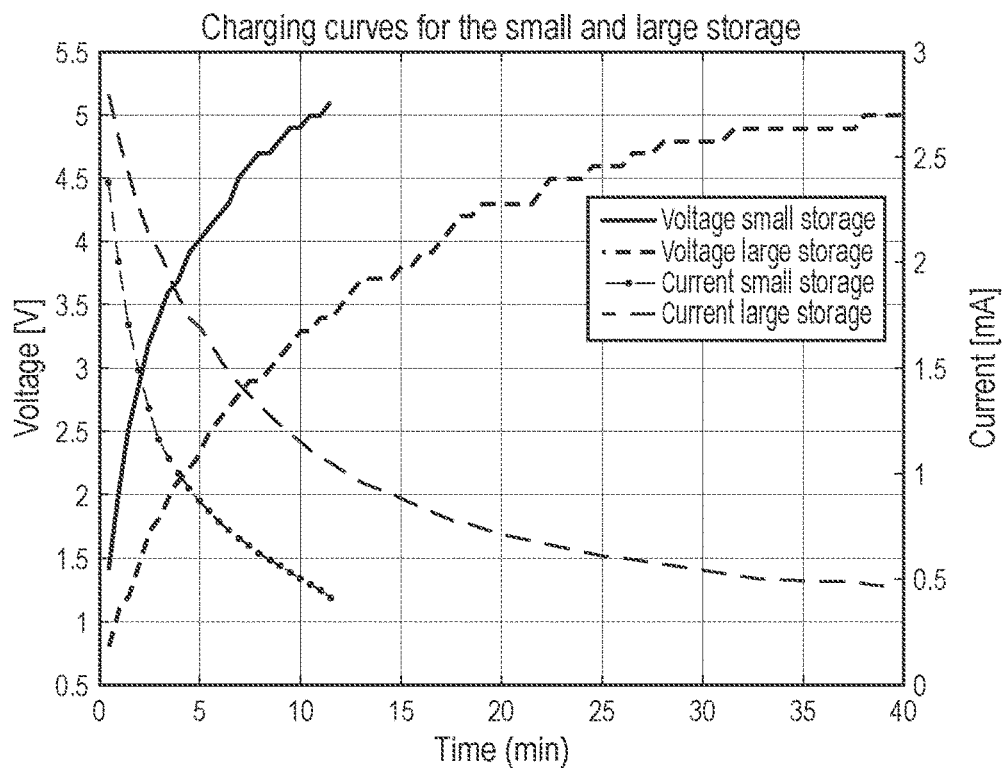
FIG. 29 is a graph illustrating charging voltage and current of two storage components of an example printed circuit board (PCB) design.

The performance of the UTET system can also be measured in terms time interval needed to recharge the storage units. The next set of experiments was conducted to evaluate the duration and the electrical quantities of the charging operations. The curves reported in FIG. 29 represent the typical voltage and current variations during the transient charging phase for both the small and large storage. From Table 3, the total capacity of the smaller storage is 147 mF (the supercapacitors are connected in parallel) and the large capacity amounts to 424 mF.

As illustrated in FIG. 29, the duration to completely charge the large and small storage, reaching 5 V across the parallel of the two capacitors, is 40 and 11.5 minutes, respectively. Generally, the storage has to be completely charged from the bottom only the first time, since in many applications, the load powered by the capacitors requires a minimum voltage, hence the storage is discharged till this value, and then it needs to be refilled. The recharges can be more frequent, but shorter in duration.

As discussed in Section 2, batteries typically remain the main solution to power medical implants. In line with this idea, the following experiments are intended to show 1) how the limitations of non-rechargeable batteries can be overcome, 2) that the U-Charge system can be equipped with a different storage element and is still able to recharge it, and 3) that a completely integrated ultrasonic feedback data channel can be embedded on the platform.

Figure 31:
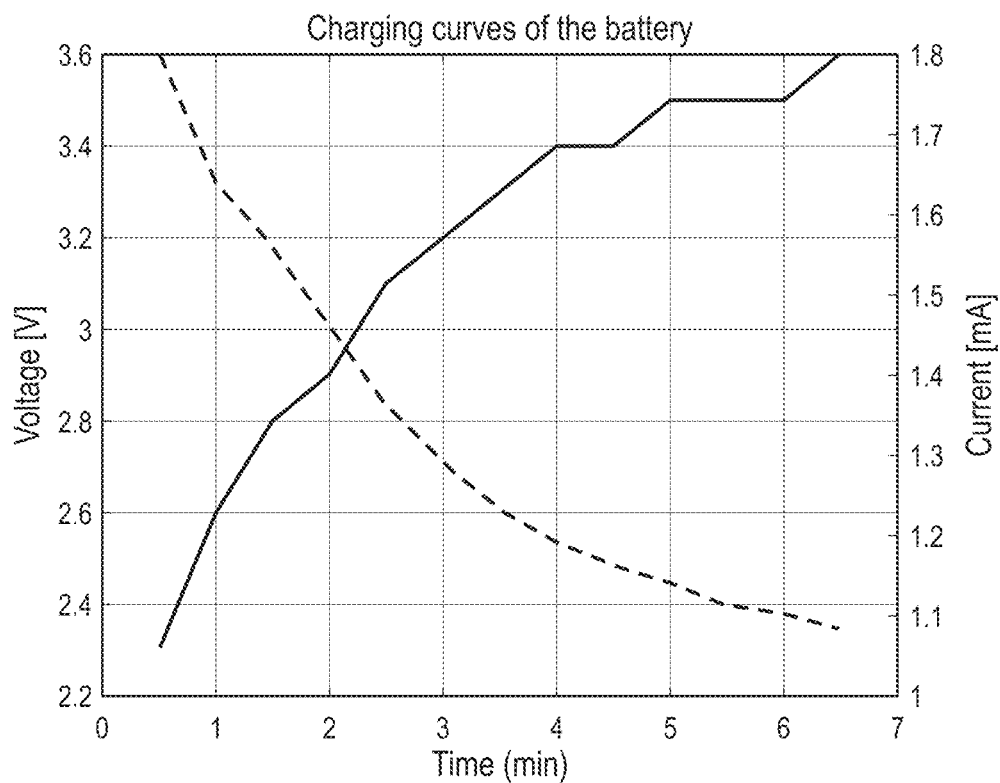
FIG. 31 is a graph illustrating charging voltage (solid line) and current (dashed line) of a PowerStream GM300910 rechargeable battery.

A PowerStream GM300910 (3.7 V, 12 mAh) battery, is one of the smallest rechargeable batteries that was selected to be tested with the UTET system. Firstly, the battery was charged by transmitting power at the FDA limit, at 700 kHz. The DC wave was obtained with the rectifier. The charging curves are shown in FIG. 31. With respect to the 147 mF storage, the time to reach the same voltage levels is double.

Figure 30:
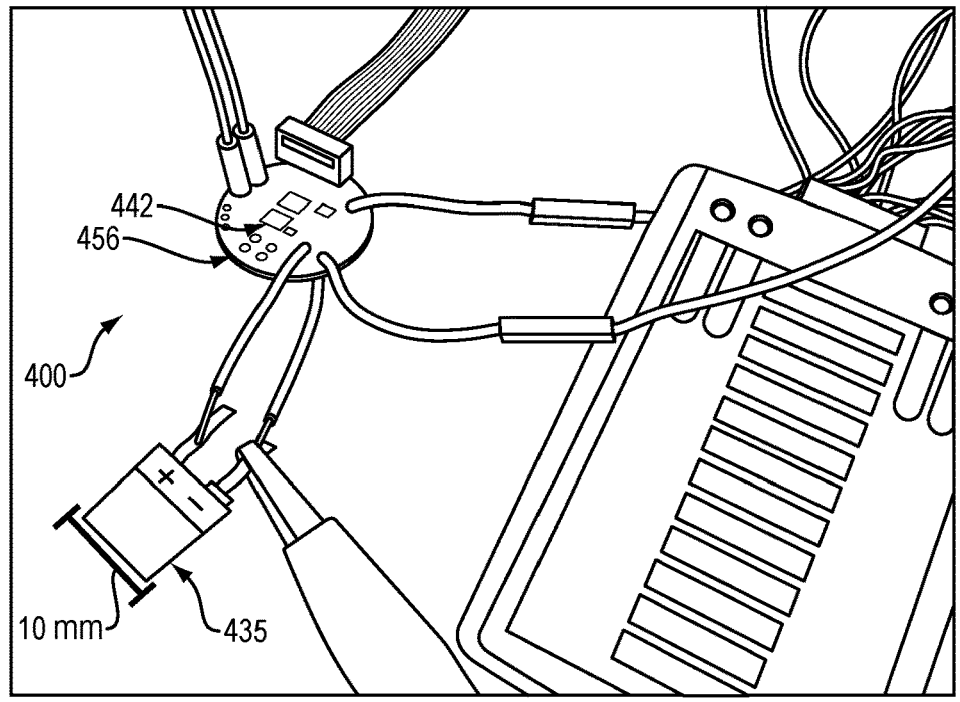
FIG. 30 illustrates an example device that includes a FPGA powered by a PowerStream GM300910 rechargeable battery.

FIG. 30 shows the test set-up 400 in which the ultrasonically recharged battery 435 is connected to a small PCB 456 containing a Lattice Semiconductor iCE40 Ultra FPGA 442. In accordance with the architecture in FIG. 12, the battery 435 is connected to the FPGA 442, which sends the waveform to the implanted PZT that, then, is used to transmit data. After the initial configuration operation of the FPGA, during the powering a voltage drop of 3.4 V and a current of 23 mA were measured. This means that the FPGA is equivalent to a resistive load of 148Ω absorbing 78.2 mW. The waveform, even though attenuated, is received after attenuation through the skin. An external receiver can be configured to implement data processing mechanism(s), and can have an analog to digital converter (ADC). The test set-up demonstrates that the implantable device can produce enough power to drive the FPGA and together with the transducer transmit information.

6—System Variant

Figure 32:
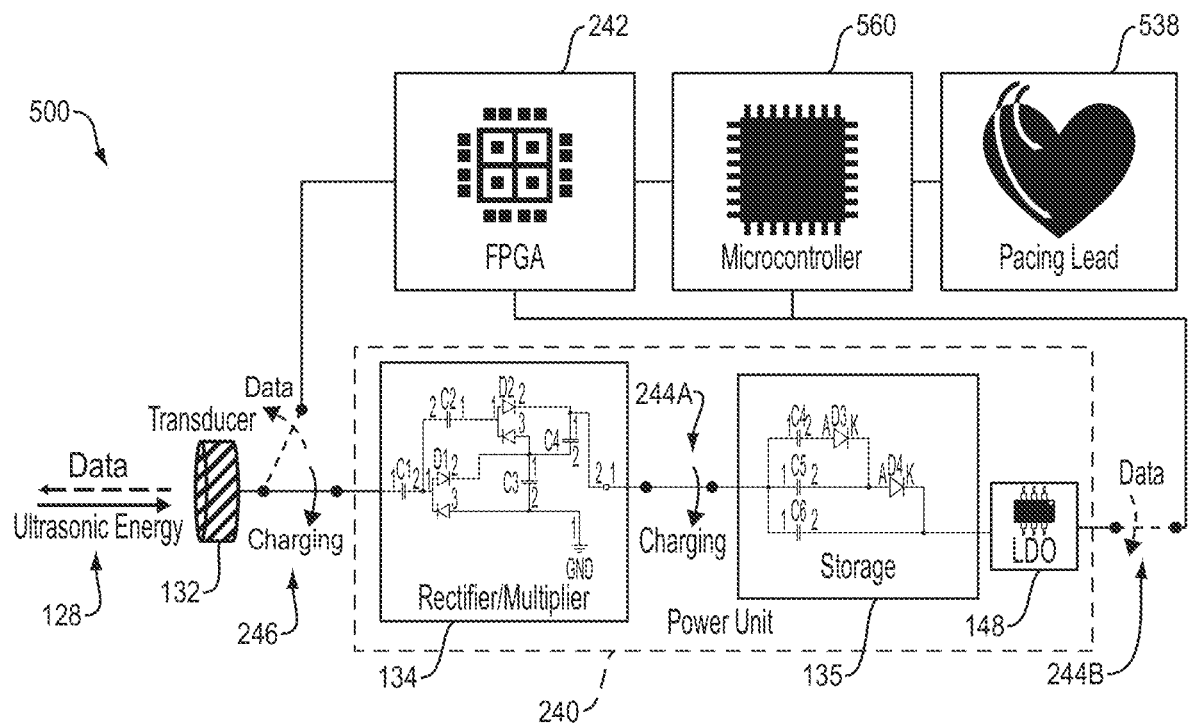
FIG. 32 is a block diagram of a reconfigurable implantable system for ultrasonic power control and telemetry configured for wireless heart pacing.

The block diagram in FIG. 32 shows a rearrangement of the basic architecture of the ultrasonic wireless system (only the implantable device is illustrated in FIG. 32). The system 500 can be expanded with a microcontroller unit (MCU) 560, as shown. The FPGA 242 included in the system 200 described above (e.g., FIG. 12) combined with a MCU 560 can offer reconfigurable and efficient data processing capabilities. The device can be configured using a control channel of the wireless communication link 128 to flexibly adapt (i) the transmission operations, such as the transmission scheme parameters to adapt to the intra-body channel conditions; (ii) the data processing operations done on the sensed data, e.g., install new processing features; (iii) the sensing and actuating operations, including the sampling frequency of the sensor. A realistic implementation can be a batteryless pacemaker. The biosensor unit 538 can include pacemaker leads. Typical load impedance of a commercial pacemaker varies between 300Ω and 1 kΩ, the minimum voltage is 2.5 V, leading to average power values of about 20 mW. Since the pacing operation is performed at a low duty-cycle for only 0.2 ms each heartbeat (i.e., approximately every second) the small storage could provide enough energy to power the device almost for an entire day (21 hours) plus other 10 hours provided by the back-up. These values are obtained bearing in mind that the supercapacitors cannot be completely depleted, since when the voltage drops to 2.5 V it is not sufficient to activate the leads. Moreover, the MCU 560 can interact with the FPGA 242 to implement pacing control algorithms or reconfigure the duty-cycle and regulate of the output pacing voltage.

7—Related Work

Denisov et al. [11] conducted a study to show the difference between ultrasonic and inductive wireless approaches to powering biomedical implants. The main result that comes from their work is that, while the inductive coupling is more performing in superficial implants (1 cm), UTET solutions work better for deep implants (10 cm). In one report [36], ultrasounds are used to directly power implanted load, and the authors claim that the system is able to transfer 100 mW of power was transferred to implanted loads and reach a peak power transfer efficiency of 39.1%. In vitro and in vivo studies have also been reported, for example in [39]. In that work, the recharging of a Li-ion battery by means of ultrasounds at a depth of 1-2 cm was demonstrated in vivo. Quantitative results show that a 4.1 V battery half depleted can be recharged with 300 mW in about 2 hours achieving an average efficiency of 20%. In many proposed systems, the energy extracted from the ultrasounds is successively used for data transmission. Hence, a communication link is created by means of different technologies. Charthad et al. [9] reported an ultrasonically rechargeable implant with a hybrid bi-directional communication link. The system has ultrasonic downlink and ultra-wideband (UWB) RF uplink. Systems that use separate technologies for wireless power transfer and data communication introduce more complexity in the system and require more precious space on the implant, especially to accommodate capacitive coils or RF antennas in addition to the acoustic transducer that can play the same role. The neurostimulator described in [29] exploits ultrasounds to recharge the battery of the implant and a data receiver circuitry to decode and process information coming from the external controller. However, physiological signals are not transmitted in the opposite direction to the on skin controller. One of the most complete works was realized in the context of the European project ULTRAsponder [49]. The system exploits ultrasonic wireless transmission for both energy transmission to the IMD and communication from the implant to the external unit. In ULTRAsponder, the communication is based on the backscattering technique, by which the external unit generates a carrier that is modulated by the implant and reflected back to the transmitter. The advantage of this principle is that the implant does not need energy for communication purposes, but the range of applications is limited, and intra-body networking is not possible, unless other nodes provides the power.

8—Conclusion

Described herein is an ultrasonic wireless system for power control and telemetry ("U-Charge"). The system provides a miniaturized UTET implantable platform for medical applications with a communication feedback data channel. Advantageously, the system uses ultrasonic waves both for powering and for data transfer.

REFERENCES

[1] Ashraf Ben Amar, Ammar B Kouki, and Hung Cao. 2015. Power Approaches for Implantable Medical Devices. Sensors 15, 11 (2015), 28889-28914.
[2] Mohammadreza Ashraf and Nasser Masoumi. 2016. A ermal Energy Harvesting Power Supply With an Internal Startup Circuit for Pacemakers. IEEE Transactions on Very Large Scale Integration (VLSI) Systems 24, 1 (2016), 26-37.
[3] Hamid Basaeri, David Christensen, Shad Roundy, Yuechuan Yu, Tram Nguyen, Prashant Tathireddy, and Darrin J Young. 2016. Ultrasonically powered hydrogel-based wireless implantable glucose sensor. In SENSORS, 2016 IEEE. IEEE, 1-3.
[4] Majid Beidaghi and Yury Gogotsi. 2014. Capacitive energy storage in micro-scale devices: recent advances in design and fabrication of micro-supercapacitors. Energy & Environmental Science 7, 3 (2014), 867-884.
[5] Kara N Bocan and Ervin Sejdic. 2016. Adaptive Transcutaneous Power Transfer to Implantable Devices: A State of the Art Review. Sensors 16, 3 (2016), 393.
[6] Wayne Burleson, Sandro Carrara, and others. 2014. Security and privacy for implantable medical devices. Springer.
[7] Andrea Cadei, Alessandro Dionisi, Emilio Sardini, and Mauro Serpelloni. 2013. Kinetic and thermal energy harvesters for implantable medical devices and biomedical autonomous sensors. Measurement Science and Technology 25, 1 (2013), 012003.
[8] Giuseppe Mario Calvagna, Giuseppe Torrisi, Clea Giuffrida, and Salvatore Patane'. 2014. Pacemaker, implantable cardioverter defibrillator, CRT, CRT-D, psychological difficulties and quality of life. International journal of cardiology 174, 2 (2014), 378-380.

[9] J. Charthad, M. J. Weber, Ting Chia Chang, M. Saadat, and A. Arbabian. 2014. A mm-sized implantable device with ultrasonic energy transfer and RF data uplink for high-power applications. In Proc. of IEEE Custom Integrated Circuits Conference (CICC),

[10] Wenwen Chen, Guozheng Yan, Shu He, an Ke, Zhiwu Wang, Hua Liu, and Pingping Jiang. 2013. Wireless powered capsule endoscopy for colon diagnosis and treatment. Physiological measurement 34, 11 (2013), 1545.

[11] Alexey Denisov and Eric Yeatman. 2010. Ultrasonic vs. inductive power delivery for miniature biomedical implants. In Body Sensor Networks (BSN), 2010 International Conference on. IEEE, 84-89.

[12] Tamara Denning, Alan Borning, Batya Friedman, Brian T Gill, Tadayoshi Kohno, and William H Maisel. 2010. Patients, pacemakers, and implantable defibrillators: Human values and security for wireless implantable medical devices. In Proceedings of the SIGCHI Conference on Human Factors in Computing Systems. ACM, 917-926.

[13] Frank D Egitto, Rabindra N Das, Glen E Thomas, and Susan Bagen. 2012. Miniaturization of electronic substrates for medical device applications. In International Symposium on Microelectronics, Vol. 2012. International Microelectronics Assembly and Packaging Society, 000186-000191.

[14] Laura Galluccio, Tommaso Melodia, Sergio Palazzo, and Giuseppe Enrico Santagati. 2012. Challenges and implications of using ultrasonic communications in intrabody area networks. In Wireless On-demand Network Systems and Services (WONS), 2012 9th Annual Conference on. IEEE, 182-189.

[15] Michael R Gold. 2015. Are Leadless Pacemakers a Niche or the Future of Device therapy? Journal of the American College of Cardiology 15, 65 (2015), 1505-1508.

[16] Freedonia Group. 2016. Medical Implants in the US—Demand and Sales Forecasts, Market Share, Market Size, Market Leaders. (2016). h p://www.freedoniagroup.com/Medical-Implants-In-e-Us.html

[17] Raffaele Guida, G Enrico Santagati, and Tommaso Melodia. 2016. A 700 kHz ultrasonic link for wireless powering of implantable medical devices. In SENSORS, 2016 IEEE. IEEE, 1-3.

[18] Mahammad A Hannan, Saad Mutashar, Salina A Samad, and Aini Hussain. 2014. Energy harvesting for the implantable biomedical devices: issues and challenges. Biomed. Eng. Online 13, 1 (2014), 79.

[19] Sco Hauck and Andre DeHon. 2010. Reconfigurable computing: the theory and practice of FPGA-based computation. Vol. 1. Morgan Kaufmann.

[20] Rangarajan Jegadeesan, Kush Agarwal, Yong-Xin Guo, Shih-Cheng Yen, and Nitish V Thakor. 2016. Wireless Power Delivery to Flexible Subcutaneous Implants Using Capacitive Coupling. IEEE Transactions on Microwave Theory and Techniques (2016).

[21] Yeun-Ho Joung. 2013. Development of implantable medical devices: from an engineering perspective. International neurourology journal 17, 3 (2013), 98-106.

[22] M Amin Karami and Daniel J Inman. 2012. Powering pacemakers from heartbeat vibrations using linear and nonlinear energy harvesters. Applied Physics Letters 100, 4 (2012), 042901.

[23] Mehdi Kiani and Maysam Ghovanloo. 2012. The circuit theory behind coupled mode magnetic resonance-based wireless power transmission. IEEE Transactions on Circuits and Systems I: Regular Papers 59, 9 (2012), 2065-2074.

[24] Albert Kim, Manuel Ochoa, Rahim Rahimi, and Babak Ziaie. 2015. New and Emerging Energy Sources for Implantable Wireless Microdevices. Access, IEEE 3 (2015), 89-98.

[25] Asimina Kiourti and Konstantina S Nikita. 2012. A review of implantable patch antennas for biomedical telemetry: Challenges and solutions [wireless corner]. IEEE Antennas and Propagation Magazine 54, 3 (2012), 210-228.

[26] Asimina Kiourti, Konstantinos A Psathas, and Konstantina S Nikita. 2014. Implantable and ingestible medical devices with wireless telemetry functionalities: A review of current status and challenges. Bioelectromagnetics 35, 1 (2014), 1-15.

[27] Chu-Pak Lau, Chung-Wah Siu, and Hung-Fat Tse. 2014. Future of implantable devices for cardiac rhythm management. Circulation 129, 7 (2014), 811-822.

[28] Bert Lenaerts and Robert Puers. 2009. Omnidirectional inductive powering for biomedical implants. Springer.

[29] Ye-Sing Luo, Jiun-Ru Wang, Wei-Jen Huang, Je-Yu Tsai, Yi-Fang Liao, Wan-Ting Tseng, Chen-Tung Yen, Pai-Chi Li, and Shen-Iuan Liu. 2013. Ultrasonic power/data telemetry and neural stimulator with OOK-PM signaling. IEEE Transactions on Circuits and Systems II: Express Briefs 60, 12 (2013), 827-831.

[30] E Meng and R Sheybani. 2014. Insight: implantable medical devices. Lab on a Chip 14, 17 (2014), 3233-3240.

[31] Giuseppina Monti, Paola Arcuti, and Luciano Tarricone. 2015. Resonant Inductive Link for Remote Powering of Pacemakers. Microwave theory and Techniques, IEEE Transactions on 63, 11 (2015), 3814-3822.

[32] K Murali, N Scianmarello, and MS Humayun. 2015. Harvesting solar energy to power ocular implants. In Biomedical Circuits and Systems Conference (BioCAS), 2015 IEEE. IEEE, 1-4.

[33] Prusayon Nintanavongsa, Ufuk Muncuk, David Richard Lewis, and Kaushik Roy Chowdhury. 2012. Design optimization and implementation for RF energy harvesting circuits. IEEE Journal on emerging and selected topics in circuits and systems 2, 1 (2012), 24-33.

[34] Jacopo Olivo, Sandro Carrara, and Giovanni De Micheli. 2011. Energy harvesting and remote powering for implantable biosensors. IEEE Sensors Journal 11, EPFL-ARTICLE-152140 (2011), 1573-1586.

[35] Shaul Ozeri and Doron Shmilovitz. 2014. Simultaneous backward data transmission and power harvesting in an ultrasonic transcutaneous energy transfer link employing acoustically dependent electric impedance modulation. Ultrasonics 54, 7 (2014), 1929-1937.

[36] Shaul Ozeri, Doron Shmilovitz, Sigmond Singer, and Chua-Chin Wang. 2010. Ultrasonic transcutaneous energy transfer using a continuous wave 650 kHz Gaussian shaded transmitter. Ultrasonics 50, 7 (2010), 666-674.

[37] Shashank Priya and Daniel J Inman. 2009. Energy harvesting technologies. Vol. 21. Springer.

[38] R Puers, Riccardo Carta, and Jef one. 2011. Wireless power and data transmission strategies for next-generation capsule endoscopes. Journal of Micromechanics and Microengineering 21, 5 (2011), 054008.

[39] Leon Radziemski and Inder Raj S Makin. 2016. In vivo demonstration of ultrasound power delivery to charge implanted medical devices via acute and survival porcine studies. Ultrasonics 64 (2016), 1-9.

[40] Smitha Rao and J-C Chiao. 2015. Body Electric: Wireless Power Transfer for Implant Applications. Microwave Magazine, IEEE 16, 2 (2015), 54-64.

[41] Mandi Rasouli and Louis Soo Jay Phee. 2010. Energy sources and their development for application in medical devices. Expert review of medical devices 7, 5 (2010), 693-709.

[42] G. E. Santagati and T. Melodia. 2017. An Implantable Low-Power Ultrasonic Platform for the Internet of Medical Things. In Proc. of IEEE Conference on Computer Communications (INFOCOM). Atlanta, USA.

[43] Ozeri Shaul and Shmilovitz Doron. 2012. Non-invasive sensing of the electrical energy harvested by medical implants powered by an ultrasonic transcutaneous energy transfer link. In Industrial Electronics (ISIE), 2012 IEEE International Symposium on. IEEE, 1153-1157.

[44] Jan Smilek and Zdenek Hadas. 2015. A study of kinetic energy harvesting for biomedical application in the head area. Microsystem Technologies (2015), 1-13.

[45] L Svilainis and G Motiejuñas. 2016. Power amplifier for ultrasonic transducer excitation. Ultragarsas "Ultrasound" 58, 1 (2016), 30-36.

[46] J-Y Tsai, K-H Huang, J-R Wang, S-I Liu, and P-C Li. 2011. Ultrasonic wireless power and data communication for neural stimulation. In Ultrasonics Symposium (IUS), 2011 IEEE International. IEEE, 1052-1055.

[47] Zian H Tseng, Robert M Hayward, Nina M Clark, Christopher G Mulvanny, Benjamin J Colburn, Philip C Ursell, Jeffrey E Olgin, Amy P Hart, and Ellen Moffatt. 2015. Sudden death in patients with cardiac implantable electronic devices. JAMA internal medicine 175, 8 (2015), 1342-1350.

[48] Erik O Udo, Norbert M van Hemel, Nicolaas P A Zuitho, Heidi Nijboer, William Taks, Pieter A Doevendans, and Karel G M Moons. 2013. Long term quality-of-life in patients with bradycardia pacemaker implantation. International journal of cardiology 168, 3 (2013), 2159-2163.

[49] ULTRAsponder. 2008. Invivo Ultrasonic Transponder System for Biomedical Applications Invivo Ultrasonic Transponder System. (2008). Retrieved 2017 Mar. 9 from http://www.ultrasponder.org/project/project.html

[50] Yang Yang, Guo Dong Xu, and Jing Liu. 2014. A prototype of an implantable thermoelectric generator for permanent power supply to body inside a medical device. Journal of Medical Devices 8, 1 (2014), 014507.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A reconfigurable implantable system for ultrasonic power control and telemetry, the system comprising:
   a) a charging device including:
      an ultrasonic transducer configured to transmit ultrasonic signals and to receive ultrasonic signals transmitted through a biological body; and
      a signal generator to drive the ultrasonic transducer to transmit an ultrasonic charging signal through the biological body; and
   b) an implantable device implantable in the biological body and configured to communicate wirelessly with the charging device through the biological body via an ultrasonic communication link between the implantable device and the charging device, the implantable device including:
      an implantable ultrasonic transducer to receive the ultrasonic charging signal from the charging device and to transmit ultrasonic signals through the biological body;
      a power unit coupled to the ultrasonic transducer, the power unit configured to harvest energy from the received ultrasonic charging signal when the implantable device is in an energy harvesting mode;
      a sensing or actuation unit powered by the harvested energy; and
      a communication unit coupled to the power unit and the sensing or actuation unit, the communication unit configured to switch the implantable device between the energy harvesting mode and an ultrasonic communication mode, the communication unit configured to read data from the sensing or actuation unit and transmit the data through the implantable ultrasonic transducer when the implantable device is in the ultrasonic communication mode.

2. The system of claim 1, wherein the power unit includes rectifying circuitry capable of converting an alternating current (AC) signal from the implantable ultrasonic transducer to a direct current (DC) signal.

3. The system of claim 2, wherein the rectifying circuitry includes a multiplier.

4. The system of claim 2, wherein the power unit includes an energy storage unit coupled to the rectifying circuitry to store the harvested energy.

5. The system of claim 4, wherein the energy storage unit includes a supercapacitor.

6. The system of claim 4, wherein the power unit includes a low drop out (LDO) regulator to limit the output voltage from the energy storage unit.

7. The system of claim 1, wherein at least one of the communication unit and the sensing or actuation unit includes programmable circuitry.

8. The system of claim 7, the programmable circuitry includes a field programmable gate array (FPGA) that is programmable via the ultrasonic communication link while the implantable device is implanted.

9. The system of claim 8, wherein the sensing or actuation unit includes or communicates with a sensor, and wherein the FPGA is programmable to control the sensor.

10. The system of claim 8, wherein the communication unit includes a microcontroller unit (MCU).

11. The system of claim 10, wherein the sensing or actuation unit includes or communicates with an actuator, and wherein the MCU is configured to control the actuator.

12. The system of claim 1, wherein the charging device is wearable on the biological body.

13. The system of claim 1, wherein the charging device is implantable in the biological body.

14. The system of claim 1, wherein the signal generator of the charging device provides an electric signal, and wherein the charging device further includes an amplifier to amplify the electric signal to drive the ultrasonic transducer of the charging device.

15. The system of claim 1, wherein the frequency of the ultrasonic charging signal is in a range of about 20 kHz to about 10 MHz.

16. The system of claim 15, wherein the ultrasonic charging signal includes a continuous sine wave.

17. The system of claim 1, wherein, after energy harvesting, the implantable device is configurable using a control channel of the ultrasonic communication link to adapt one or more of (i) ultrasonic transmission operations, (ii) data processing operations performed on the data, and (iii) sensing operations performed by the sensing or actuation unit.

18. The system of claim 1, wherein, after energy harvesting, the implantable device is configurable using a control channel of the ultrasonic communication link to adapt ultrasonic transmission operations by changing the transmission scheme parameters to adapt to the intra-body channel conditions.

19. The system of claim 1, wherein, after energy harvesting, the implantable device is configurable using a control channel of the ultrasonic communication link to adapt data processing operations by performing one or more of modifying processing features and extracting new physiological parameters from the data.

20. The system of claim 1, wherein, after energy harvesting, the implantable device is configurable using a control channel of the ultrasonic communication link to adapt sensing operations by changing the sampling frequency of a sensor or the sensing resolution of the sensor.

21. The system of claim 1, wherein the system comprises plural implantable devices.

22. A method for ultrasonic power control and telemetry, the method comprising:
   a) transmitting ultrasonic signals through a biological body via an ultrasonic communication link between a charging device and an implantable device implanted in the biological body; and
   b) with an ultrasonic transducer of the implantable device, receiving an ultrasonic charging signal from the charging device;
   c) harvesting energy from the received ultrasonic charging signal when the implantable device is in an energy harvesting mode;
   d) powering a sensing or actuation unit of the implantable device with the harvested energy;
   e) reading data from the sensing or actuation unit and transmitting the data through the ultrasonic transducer of the implantable device when the implantable device is in the ultrasonic communication mode; and
   f) switching the implantable device between the energy harvesting mode and the ultrasonic communication mode.

23. The method of claim 22, further comprising, in the charging device, driving an ultrasonic transducer to transmit the ultrasonic charging signal through the biological body.

24. The method of claim 22, further comprising, in the implantable device, converting an alternating current (AC) signal output from the ultrasonic transducer to a direct current (DC) signal using rectifying circuitry.

25. The method of claim 24, further comprising storing the harvested energy in an energy storage unit of the implantable device.

26. The method of claim 22, further comprising programming a field programmable gate array (FPGA) of the implantable device via the ultrasonic communication link while the implantable device is implanted.

27. The method of claim 22, further comprising, after energy harvesting, configuring the implantable device using a control channel of the ultrasound communication link to adapt one or more of (i) ultrasonic transmission operations, (ii) data processing operations performed on the data, and (iii) sensing operations performed by the sensing or actuation unit.

28. A reconfigurable implantable device for ultrasonic power control and telemetry, the implantable device implantable in a biological body and configured to communicate wirelessly with a charging device through the biological body via an ultrasonic communication link between the implantable device and the charging device, the implantable device comprising:
   an implantable ultrasonic transducer to receive an ultrasonic charging signal from the charging device and to transmit ultrasonic signals through the biological body;
   a power unit coupled to the ultrasonic transducer, the power unit configured to harvest energy from the received ultrasonic charging signal when the implantable device is in an energy harvesting mode;
   a sensing or actuation unit powered by the harvested energy; and
   a communication unit coupled to the power unit and the sensing or actuation unit, the communication unit configured to switch the implantable device between the energy harvesting mode and an ultrasonic communication mode, the communication unit configured to read data from the sensing or actuation unit and transmit the data through the implantable ultrasonic transducer when the implantable device is in the ultrasonic communication mode.

29. The device of claim 28, wherein at least one of the communication unit and the sensing or actuation unit includes a field programmable gate array (FPGA) that is programmable via the ultrasonic communication link while the implantable device is implanted.

30. The device of claim 29, wherein the sensing or actuation unit includes or communicates with a sensor, and wherein the FPGA is programmable to control the sensor.

31. The device of claim 30, wherein the sensing or actuation unit includes or communicates with an actuator, and wherein the communication unit includes a microcontroller unit (MCU) configured to control the actuator.

32. The device of claim 28, wherein, after energy harvesting, the implantable device can be configured using a control channel of the ultrasonic communication link to adapt one or more of (i) ultrasonic transmission operations, (ii) data processing operations performed on the data, and (iii) sensing operations performed by the sensing or actuation unit.

* * * * *